US010123848B2

(12) United States Patent  
Lawrence et al.

(10) Patent No.: US 10,123,848 B2  
(45) Date of Patent: Nov. 13, 2018

(54) EUS FIDUCIAL NEEDLE STYLET HANDLE ASSEMBLY

(71) Applicant: Cook Medical Technologies LLC, Bloomington, IN (US)

(72) Inventors: Andrea C. Lawrence, Winston-Salem, NC (US); Margaret R. Widmyer, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 296 days.

(21) Appl. No.: 14/950,184

(22) Filed: Nov. 24, 2015

(65) Prior Publication Data

US 2016/0166330 A1 Jun. 16, 2016

Related U.S. Application Data

(60) Provisional application No. 62/086,927, filed on Dec. 3, 2014.

(51) Int. Cl.
*A61B 17/34* (2006.01)
*A61B 90/00* (2016.01)
*A61M 37/00* (2006.01)

(52) U.S. Cl.
CPC .......... *A61B 90/39* (2016.02); *A61B 17/3468* (2013.01); *A61M 37/0069* (2013.01);
(Continued)

(58) Field of Classification Search
CPC .......... A61B 17/3468; A61B 2017/347; A61B 2090/033; A61B 2090/034;
(Continued)

(56) References Cited

U.S. PATENT DOCUMENTS 2,009,393 A 7/1936 Failla
2,239,963 A 4/1941 Hoffert
(Continued)

FOREIGN PATENT DOCUMENTS

EP 0 093 101 A2 11/1983
EP 1 518 549 A1 3/2005
(Continued)

OTHER PUBLICATIONS

International Search Report and Written Opinion for International PCT No. PCT/US2015/062351, dated Feb. 15, 2016, pp. 1-11.
(Continued)

*Primary Examiner* — Ryan J Severson

(74) *Attorney, Agent, or Firm* — Brinks Gilson & Lione

(57) ABSTRACT

A safety-catch mechanism for a fiducial-deployment system, having a main handle, a stylet, a guide sleeve, and a grasping handle for moving adjacent to the guide sleeve. One of the guide sleeve or grasping handle has a threaded surface, and the other has one or more protruding tabs to rotatably engage between the threads. A safety-catch structure is located between the threads and configured to resist rotation of the grasping handle when one of the protruding tabs contacts this structure, unless the user applies a threshold amount of mechanical force to overcome this safety-catch structure, permitting distal movement of the stylet.

20 Claims, 12 Drawing Sheets

(52) U.S. Cl.
CPC ... *A61B 2090/034* (2016.02); *A61B 2090/035* (2016.02); *A61B 2090/0811* (2016.02); *A61B 2090/3912* (2016.02); *A61B 2090/3925* (2016.02); *A61B 2090/3966* (2016.02); *A61B 2090/3987* (2016.02)

(58) Field of Classification Search
CPC ...... A61B 2090/035; A61B 2090/0811; A61B 2090/363; A61B 2090/3904; A61B 2090/3908; A61B 2090/3912; A61B 2090/3916; A61B 2090/3925; A61B 2090/3966; A61B 2090/3987; A61B 90/39; A61M 37/0069
See application file for complete search history.

(56) References Cited

U.S. PATENT DOCUMENTS

| | | | |
|---|---|---|---|
| 2,269,963 A | 1/1942 | Wappler | |
| 2,620,796 A | 12/1952 | Eriksen et al. | |
| 3,470,834 A | 10/1969 | Bone | |
| 3,815,798 A | 6/1974 | Lavitch et al. | |
| 3,820,545 A | 6/1974 | Jefferts | |
| 4,086,914 A | 5/1978 | Moore | |
| 4,105,030 A | 8/1978 | Kercso | |
| 4,154,239 A | 5/1979 | Turley | |
| 4,451,254 A | 5/1984 | Dinius et al. | |
| 4,646,740 A | 3/1987 | Peters et al. | |
| 4,648,542 A | 3/1987 | Fox et al. | |
| 4,661,103 A | 4/1987 | Harman | |
| 4,700,692 A | 10/1987 | Baumgartner | |
| 4,716,901 A | 1/1988 | Jackson et al. | |
| 4,807,628 A | 2/1989 | Peters et al. | |
| 4,976,686 A | 12/1990 | Ball et al. | |
| 5,002,548 A | 3/1991 | Campbell et al. | |
| 5,024,727 A | 6/1991 | Campbell et al. | |
| 5,047,038 A | 9/1991 | Peters et al. | |
| 5,281,197 A | 1/1994 | Arias et al. | |
| 5,669,543 A | 9/1997 | Ueno | |
| 5,755,726 A | 5/1998 | Pratt et al. | |
| 5,810,769 A | 9/1998 | Schlegel et al. | |
| 5,860,909 A | 1/1999 | Mich et al. | |
| 6,004,320 A | 12/1999 | Casscells et al. | |
| 6,186,144 B1 | 2/2001 | Davis et al. | |
| 6,210,315 B1 | 4/2001 | Andrews et al. | |
| 6,220,248 B1 | 4/2001 | Voegele et al. | |
| 6,221,003 B1 | 4/2001 | Sierocuk et al. | |
| 6,228,055 B1 | 5/2001 | Foerster et al. | |
| 6,264,599 B1 | 7/2001 | Slater et al. | |
| 6,267,718 B1 | 7/2001 | Vitali et al. | |
| 6,283,948 B1 | 9/2001 | McKernan et al. | |
| 6,347,241 B2 | 2/2002 | Burbank et al. | |
| 6,402,677 B1 | 6/2002 | Jacobs | |
| 6,432,035 B1 | 8/2002 | Ravins et al. | |
| 6,450,938 B1 | 9/2002 | Miller | |
| 6,569,077 B2 | 5/2003 | Schmidt | |
| 6,592,508 B1 | 7/2003 | Ravins et al. | |
| 6,613,002 B1 | 9/2003 | Clark et al. | |
| 6,796,935 B1 | 9/2004 | Savino | |
| 6,824,507 B2 | 11/2004 | Miller | |
| 6,837,844 B1 | 1/2005 | Ellard et al. | |
| 6,889,833 B2 | 5/2005 | Seiler et al. | |
| 6,976,955 B2* | 12/2005 | Hardin .................. | A61B 10/04 600/131 |
| 7,001,341 B2 | 2/2006 | Gellman et al. | |
| 7,008,368 B2 | 3/2006 | Terwilliger et al. | |
| 7,041,048 B2 | 5/2006 | Drobnik et al. | |
| 7,083,566 B2 | 8/2006 | Tornes et al. | |
| 7,104,945 B2 | 9/2006 | Miller | |
| 7,144,386 B2 | 12/2006 | Korkor et al. | |
| 7,214,206 B2 | 5/2007 | Rue et al. | |
| 7,247,160 B2 | 7/2007 | Seiler et al. | |
| 7,280,865 B2 | 10/2007 | Adler | |
| 7,335,155 B2 | 2/2008 | Chu | |
| 7,361,135 B2 | 4/2008 | Drobnik et al. | |
| 7,407,054 B2 | 8/2008 | Seiler et al. | |
| 7,429,240 B2 | 9/2008 | Miller | |
| 7,465,279 B2 | 12/2008 | Beckman et al. | |
| 7,510,549 B2 | 3/2009 | Rue et al. | |
| 7,565,191 B2 | 7/2009 | Burbank et al. | |
| 7,577,473 B2 | 8/2009 | Davis et al. | |
| 7,588,528 B2 | 9/2009 | Drobnik et al. | |
| 7,615,076 B2 | 11/2009 | Cauthen, II et al. | |
| 7,651,505 B2 | 1/2010 | Lubock et al. | |
| 7,736,343 B2 | 6/2010 | Marshall et al. | |
| 7,819,820 B2 | 10/2010 | Field et al. | |
| 7,850,639 B2 | 12/2010 | Rue et al. | |
| 7,927,271 B2* | 4/2011 | Dimitriou ........... | A61B 1/00128 600/104 |
| 7,945,307 B2* | 5/2011 | Lubock ............... | A61B 17/3468 128/899 |
| 8,728,040 B2* | 5/2014 | Beller ................. | A61M 5/2033 604/137 |
| 8,838,208 B2* | 9/2014 | Lavelle .............. | A61B 17/3468 600/431 |
| 8,855,747 B2* | 10/2014 | Murray ............... | A61N 5/1001 600/414 |
| 9,042,964 B2* | 5/2015 | Ducharme ......... | A61B 17/3468 600/426 |
| 9,072,542 B2* | 7/2015 | Ducharme ......... | A61B 17/3468 |
| 9,522,264 B2* | 12/2016 | Clancy .............. | A61M 37/0069 |
| 9,638,770 B2* | 5/2017 | Dietz ................. | G01R 33/286 |
| 9,770,262 B2* | 9/2017 | Clancy .............. | A61B 17/3468 |
| 2003/0120141 A1 | 6/2003 | Adler | |
| 2003/0233101 A1 | 12/2003 | Lubock et al. | |
| 2003/0233126 A1 | 12/2003 | Kaplan et al. | |
| 2004/0097780 A1 | 5/2004 | Otsuka | |
| 2004/0236213 A1 | 11/2004 | Jones et al. | |
| 2004/0260199 A1 | 12/2004 | Hardia, Jr. et al. | |
| 2004/0260274 A1* | 12/2004 | Hardin .................. | A61B 10/04 606/1 |
| 2005/0038355 A1 | 2/2005 | Gellman et al. | |
| 2005/0267319 A1 | 12/2005 | White et al. | |
| 2006/0058569 A1 | 3/2006 | Chu | |
| 2006/0173236 A1 | 8/2006 | White et al. | |
| 2006/0235298 A1 | 10/2006 | Kotmel et al. | |
| 2007/0093726 A1 | 4/2007 | Leopold et al. | |
| 2007/0167736 A1 | 7/2007 | Dietz et al. | |
| 2007/0270640 A1 | 11/2007 | Dmitriou et al. | |
| 2008/0033280 A1 | 2/2008 | Lubock et al. | |
| 2008/0033286 A1 | 2/2008 | Whitmore et al. | |
| 2008/0243148 A1 | 10/2008 | Mikkaichi et al. | |
| 2008/0269688 A1 | 10/2008 | Colucci et al. | |
| 2008/0287782 A1 | 11/2008 | Traboulsi et al. | |
| 2009/0018439 A1 | 1/2009 | Jones et al. | |
| 2009/0105518 A1 | 4/2009 | Schreiber et al. | |
| 2009/0105584 A1 | 4/2009 | Jones | |
| 2009/0131734 A1 | 5/2009 | Neustadter et al. | |
| 2009/0209804 A1 | 8/2009 | Seiler et al. | |
| 2009/0227893 A1 | 9/2009 | Coonahan et al. | |
| 2010/0010342 A1 | 1/2010 | Burbank et al. | |
| 2010/0036241 A1 | 2/2010 | Mayse et al. | |
| 2010/0042041 A1 | 2/2010 | Tune et al. | |
| 2010/0063392 A1 | 3/2010 | Nishina et al. | |
| 2010/0137891 A1 | 6/2010 | Shalon et al. | |
| 2010/0280367 A1 | 11/2010 | Ducharme et al. | |
| 2010/0331677 A1 | 12/2010 | Hong et al. | |
| 2011/0028831 A1 | 2/2011 | Kent | |
| 2011/0071424 A1 | 3/2011 | Nock et al. | |
| 2011/0152611 A1 | 6/2011 | Ducharme et al. | |
| 2011/0288581 A1 | 11/2011 | Paul, Jr. et al. | |
| 2011/0319864 A1 | 12/2011 | Beller et al. | |
| 2012/0265042 A1 | 10/2012 | Neinast et al. | |
| 2013/0006101 A1 | 1/2013 | McHugo et al. | |
| 2013/0006286 A1 | 1/2013 | Lavelle et al. | |
| 2013/0096427 A1 | 4/2013 | Murray et al. | |
| 2014/0121677 A1 | 5/2014 | Clancy et al. | |
| 2014/0221971 A1* | 8/2014 | Beller ................. | A61M 5/2033 604/506 |

(56) References Cited

U.S. PATENT DOCUMENTS

| | | | | |
|---|---|---|---|---|
| 2014/0243844 | A1* | 8/2014 | Clancy | A61M 37/0069 |
| | | | | 606/117 |
| 2015/0351862 | A1* | 12/2015 | Clancy | A61B 17/3468 |
| | | | | 600/424 |
| 2016/0166330 | A1* | 6/2016 | Lawrence | A61B 19/54 |
| | | | | 606/116 |

FOREIGN PATENT DOCUMENTS

| | | | |
|---|---|---|---|
| EP | 2 719 355 | A2 | 4/2014 |
| FR | 2 762 517 | A1 | 4/1997 |
| JP | 6323312 | | 11/1994 |
| JP | 2013514142 | A | 4/2013 |
| WO | WO 97/19724 | A1 | 6/1997 |
| WO | WO 01/00101 | A1 | 1/2001 |
| WO | WO 2006/012630 | A2 | 2/2006 |
| WO | WO 2007/094001 | A2 | 8/2007 |
| WO | WO 2007/103204 | A2 | 9/2007 |
| WO | WO 2008/016551 | A1 | 2/2008 |
| WO | WO 2009/100106 | A1 | 8/2009 |
| WO | WO 2009/132349 | A2 | 10/2009 |
| WO | WO 2010/126750 | A2 | 11/2010 |
| WO | WO 2012/152666 | A1 | 11/2012 |
| WO | WO 2014/133777 | A1 | 9/2014 |

OTHER PUBLICATIONS

International Search Report for International Application No. PCT/US2010/059641, dated May 25, 2011, 5 pages.

International Search Report for International Application No. PCT/US2012/058679, dated Jan. 2, 2013, 3 pages.

International Search Report for International Application No. PCT/US2013/023401, dated May 7, 2013, 2 pages.

International Search Report for International Application No. PCT/US2014/016218, dated Apr. 4, 2014, 3 pages.

Marker Kit, "Gold fiducial markers—Accurate localization for soft tissue targets," Best Medical International, Inc. Springfield, VA, Jan. 2008, pp. 42-54.

PCT Notification of Transmittal of the International Search Report and Written Opinion of the International Search Authority, or the Declaration for PCT Application No. PCT/US2010/031842, dated May 6, 2010.

Partial European Patent Office Search Report for European Patent No. EP 2 719 355 A3, dated Apr. 10, 2014, (5 pages).

Australian Office Action dated Dec. 5, 2017, for Australian Patent Application No. 2015355303, (3 pages).

Japanese Office Action dated Jun. 5, 2018, for Japanese Patent Application No. 2017-529679, (4 pages).

* cited by examiner

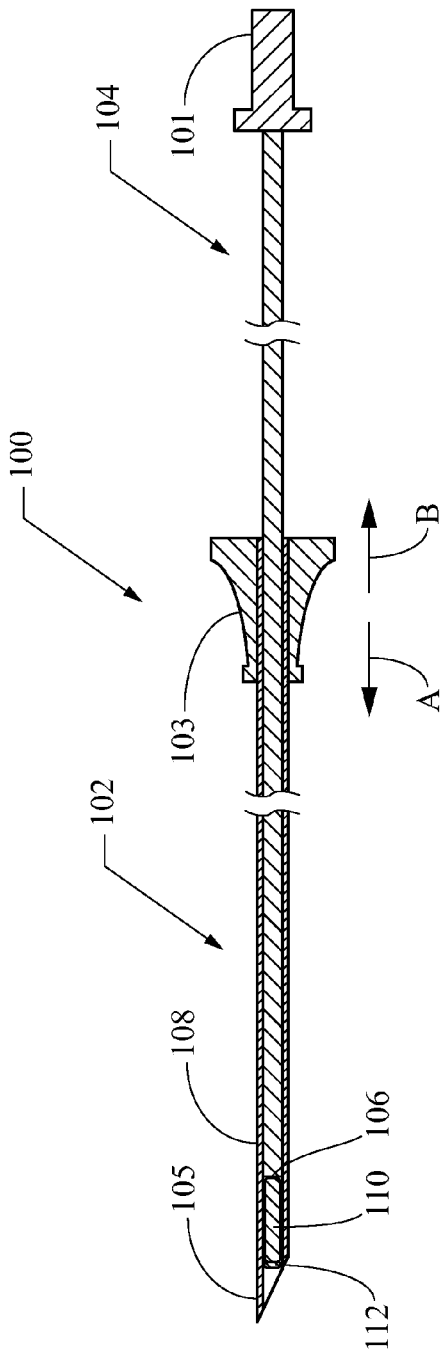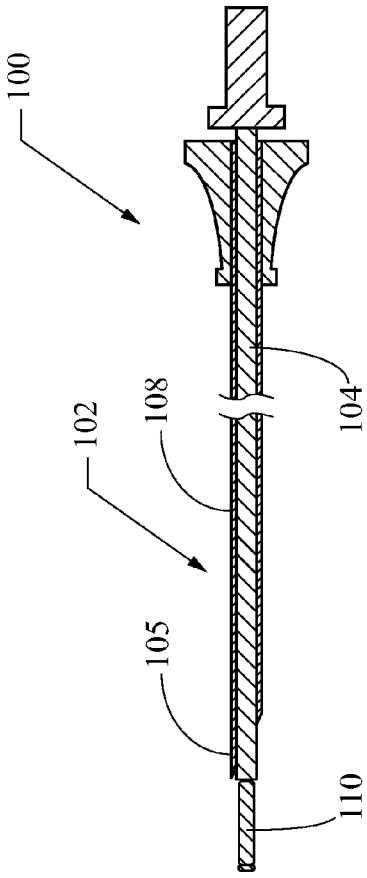
FIG. 1A (Prior Art)
FIG. 1B (Prior Art)

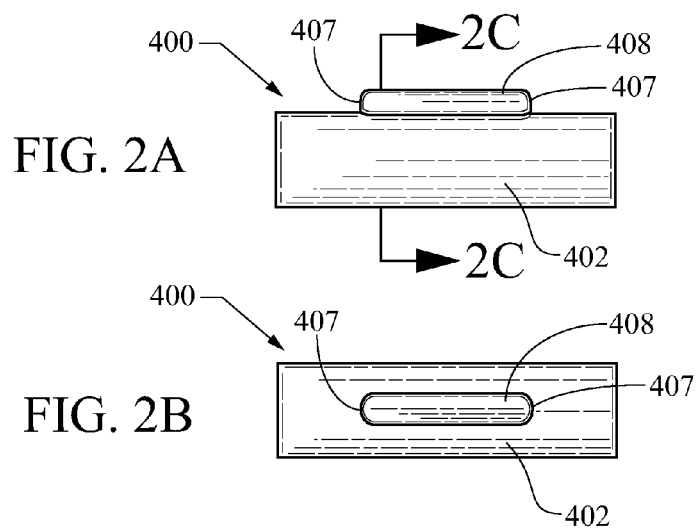
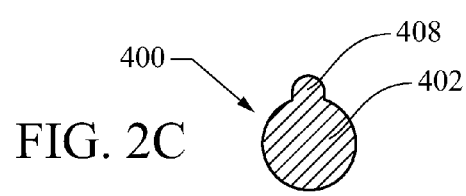
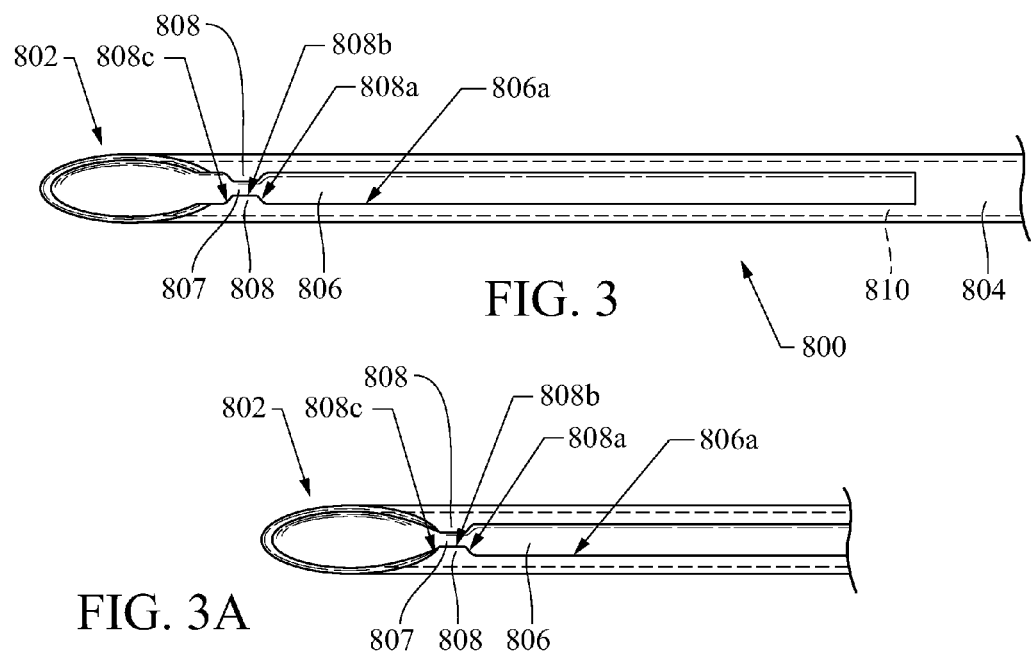

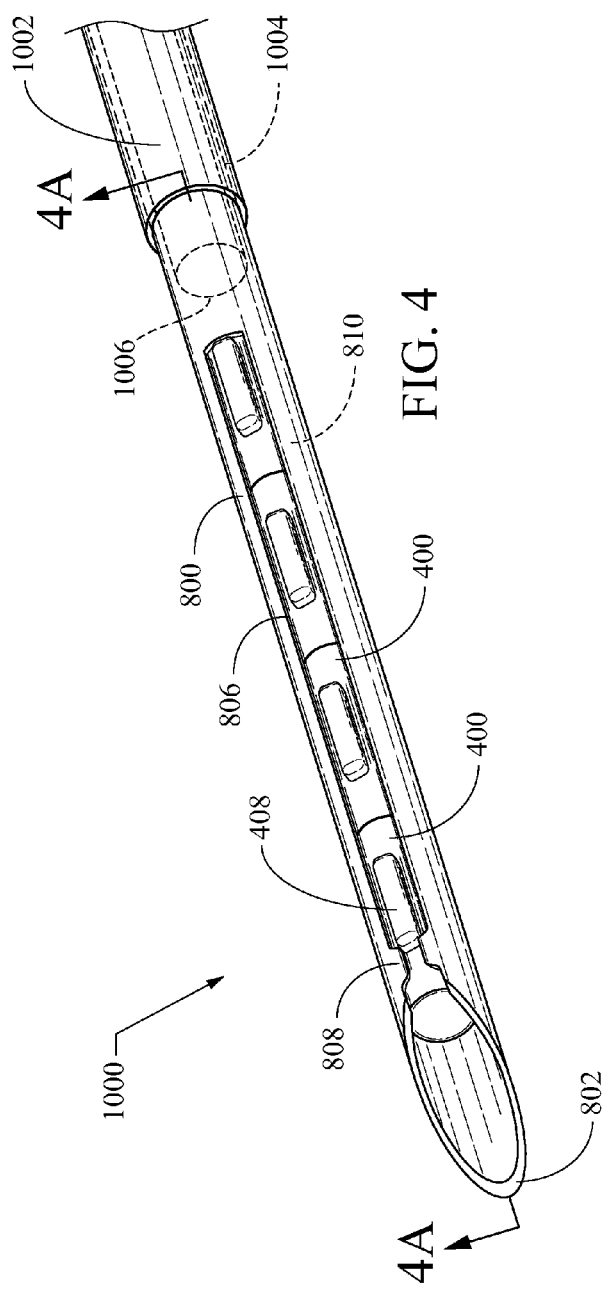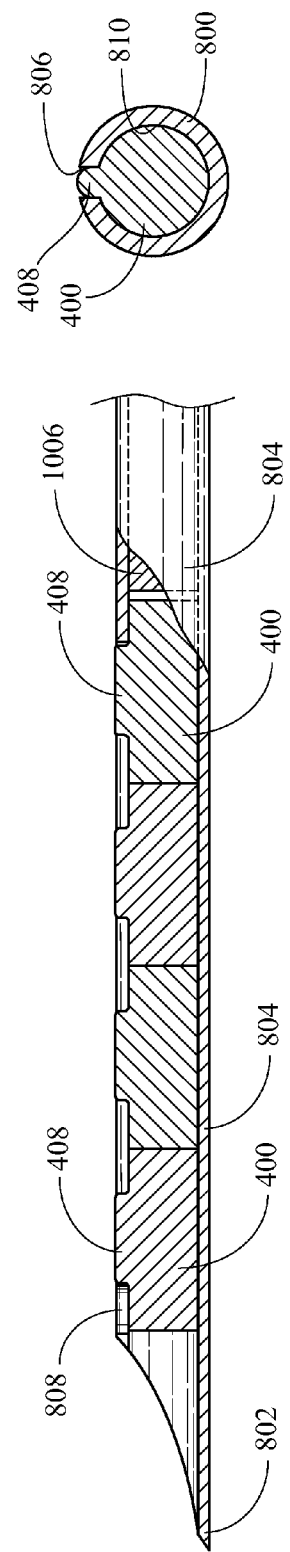
FIG. 4
FIG. 4A
FIG. 4B

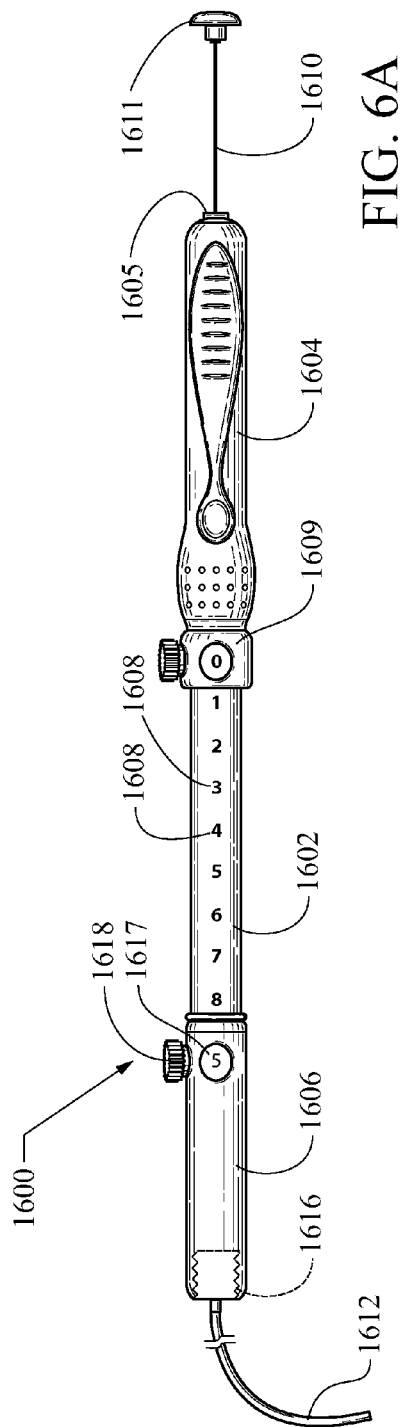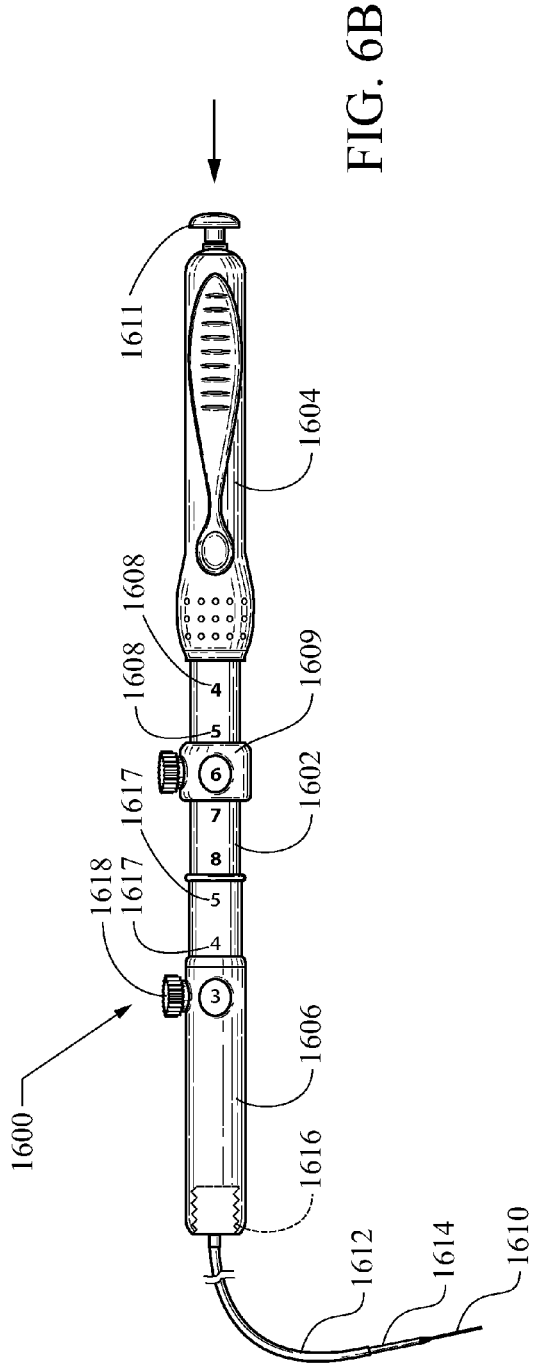
FIG. 6A
FIG. 6B

EUS FIDUCIAL NEEDLE STYLET HANDLE ASSEMBLY

CROSS-REFERENCE TO RELATED APPLICATION

This application claims priority to U.S. Provisional Application No. 62/086,927, filed with the U.S. Patent and Trademark Office on Dec. 3, 2014, the entirety of which is hereby incorporated herein by reference.

TECHNICAL FIELD

Embodiments disclosed herein relate generally to a medical device system including one or more fiducials and methods of use for same. More particularly, the disclosed embodiments pertain to handle mechanisms and systems including same for deploying fiducials, and methods of use for same.

BACKGROUND

Medical procedures often require locating and treating target areas within a patient. Focused, dose-delivery radiation therapy requires locating the target with a high degree of precision to limit damaging healthy tissue around the target. It is particularly important to know or estimate the precise location of the target in radiation oncology because it is desirable to limit the exposure of adjacent body parts to the radiation in a patient already suffering the depredations of cancer. However, in all treatment procedures, whether radiologic or otherwise, it is most desirable to be able to accurately target a region to be treated.

In many applications, it is not possible to directly view a treatment target or portion thereof (such as, for example, a cancerous tumor, cyst, pseudocyst, or other target) that needs to be acted on in some manner. As one example, when treating a lung or pancreatic tumor with radiation, it may not possible to view the actual tumor within the patient immediately before the radiation treatment. It is therefore highly advantageous to have some mechanism for permitting the tumor to be located accurately so that the radiation treatment can be targeted at the tumor while avoiding damage to healthy tissue.

Even for target regions that may be visualized using CAT (computer-assisted tomography) scans, MRI (magnetic resonance imaging), x-rays, ultrasound, or other techniques, difficulties often arise in targeting a treatment. This is particularly true for target regions within a torso of a patient and soft tissue regions. Due to the mobility of tissues in those regions (e.g., movement of internal organs during respiration and/or digestion, the movement of breast tissue with any change of body position, etc.), a target region may not remain fixed relative to anatomical landmarks and/or to marks that can be placed onto an external surface of a patient's body during one of those visualization procedures.

Several techniques have been developed to address this problem. One such technique is to place markers into the patient along the margins of the target region. The markers may be active (e.g., emitting some kind of signal useful in targeting a therapy) or passive (e.g., non-ferromagnetic metallic markers—called fiducials—that can be used for targeting under ultrasound, MRI, x-ray, or other targeting techniques, which may be included in a treatment device).

A fiducial is typically formed of a radio-opaque material that the target can be effectively located and treated with a device that targets a site using the fiducials as positional markers under radiographic detection. Typically, the fiducials may be inserted into the patient during a simple operation. Percutaneous placement is most commonly used. However, use of minimally-invasive placement via an endoscope has recently developed for fiducial placement into a patient's internal organs. For example, percutaneous placement of fiducials along the margins of a pancreatic tumor can be complex and painful (particularly for obese patients, where the needle size is necessarily larger). Another process using percutaneously implanted objects in a patient is brachytherapy. In brachytherapy, radioactive sources or "seeds" are implanted into and/or adjacent a tumor to provide a high dose of radiation to the tumor, but not the healthy tissue surrounding the tumor.

FIGS. 1A and 1B show longitudinal sectional views of a two-piece introducer 100 of the prior art useful for placement of brachytherapy seeds or fiducials. Referring first to FIG. 1A, the introducer 100 includes a needle 102 and a stylet 104 slidably disposed within the needle 102. The stylet 104 includes a first handle 101 and a blunt distal end 106. The needle 102 includes a second handle 103 and a bevel-tipped cannula 108 extending through the second handle 103. The cannula 108 is configured to hold a seed/fiducial 110. The cannula 108 has a distal tip 105 configured for percutaneous implantation of the seed/fiducial 110 into the patient.

In a "pre-loaded configuration," the seed/fiducial 110 is retained in the cannula 108 by a plug 112 made from bone wax or other suitable bio-compatible material(s). This is typically accomplished by a "muzzle-loading" technique where the fiducial is placed into the distal needle and then held in place by the bone wax plug. This can present some challenges, as the bone wax plug 112 can be visible as an artifact in the patient, potentially interfering with clear visualization of body structures or treatment devices. With this configuration, the cannula 108 must be withdrawn and reloaded after delivery of each seed/fiducial 110. If the target locations for the fiducials are very far apart, use of a single percutaneous introducer cannula/trocar for multiple introductions of the cannula 108 may not be possible. In such a circumstance, the patient must endure several percutaneous punctures (and the increased attendant risk of infection for each).

To implant the desired arrangement of seeds/fiducials 110 at a target location in a patient, an operator pushes the cannula 108 in a first direction (arrow A) to insert the tip 105 into the patient (typically under fluoroscopic visualization). The operator then pushes the second handle 103 further in the first direction to position the tip 105 at the desired depth within the patient where a seed/fiducial 110 is to be implanted. Throughout this motion, the operator moves the needle 102 and the stylet 104 together as a unit. At the desired depth/location, the operator grasps the first handle 101 with one hand and the second handle 103 with the other hand. Then, the operator holds the first handle 101 stationary while simultaneously sliding the second handle 103 back in a second direction (arrow B) toward the first handle 101. As shown in FIG. 1B, this movement causes the cannula 108 to retract over the seed/fiducial 110 to implant it in the patient. Alternatively, the operator may move the first handle 101 in the first direction (arrow A) while sliding the second handle 103 back in the second direction (arrow B). This causes the stylet 104 to push the seeds 110 out of the cannula 108. The procedure is then repeated to place other seeds/fiducials 110. When being used for targeting of radiation therapy, a minimum of three fiducials is typically required.

One potential issue that may arise is the premature deployment of fiducials. This may occur prior to the user deploying the fiducial(s) at a target site, for example if the stylet 104 undergoes inadvertent distal movement relative to the cannula 108. Premature deployment of fiducials may occur during manufacturing, shipping, or handling immediately prior to use, to name a few common examples. Solutions to this problem may also have practical limitations, for example, certain structures may not be feasible or cost effective given certain manufacturing environments (e.g., molding vs. 3D printing) and materials (e.g., plastics vs. metals).

It would be desirable to use ultrasound, and particularly endoscopic ultrasound (EUS) for navigation and placement of fiducials. As such it would be desirable to provide and use the largest possible fiducial that will provide improved echogenicity based on its size and echogenic profile. It would be desirable to provide multiple fiducials in a needle that can be introduced in a controlled serial manner (one, or some other pre-determined number, at a time) rather than requiring manual reloading after placement of each fiducial. It would further be desirable to provide such a system with features that will effectively prevent premature and/or undesired fiducial deployment.

BRIEF SUMMARY

Embodiments of a safety-catch mechanism for a fiducial deployment system described herein may include a mechanism to avoid premature or inadvertent deployment of fiducials. The mechanism may include a safety-catch structure located between threads of a threaded surface, designed to prevent mating threads from freely rotating over the threaded surface. A user may be able to overcome this structure by applying a threshold level of mechanical force. Once overcome, the fiducial deployment system may be unlocked and fiducials may be deployed.

BRIEF DESCRIPTION OF THE DRAWINGS

FIGS. 1A-1B show a prior art fiducial introducer and method of use;

FIGS. 2A-2C show an embodiment of a fiducial from, respectively, top, side, and transverse section views;

FIG. 3 shows a top view of a slotted needle embodiment;

FIG. 3A shows a top view of another slotted needle embodiment;

FIGS. 4-4B show, respectively, a top perspective view, a longitudinal section view, and a transverse section view of a distal fiducial deployment system portion;

FIGS. 6A-6B show a handle embodiment for a fiducial deployment system;

DETAILED DESCRIPTION

Figure 5A:
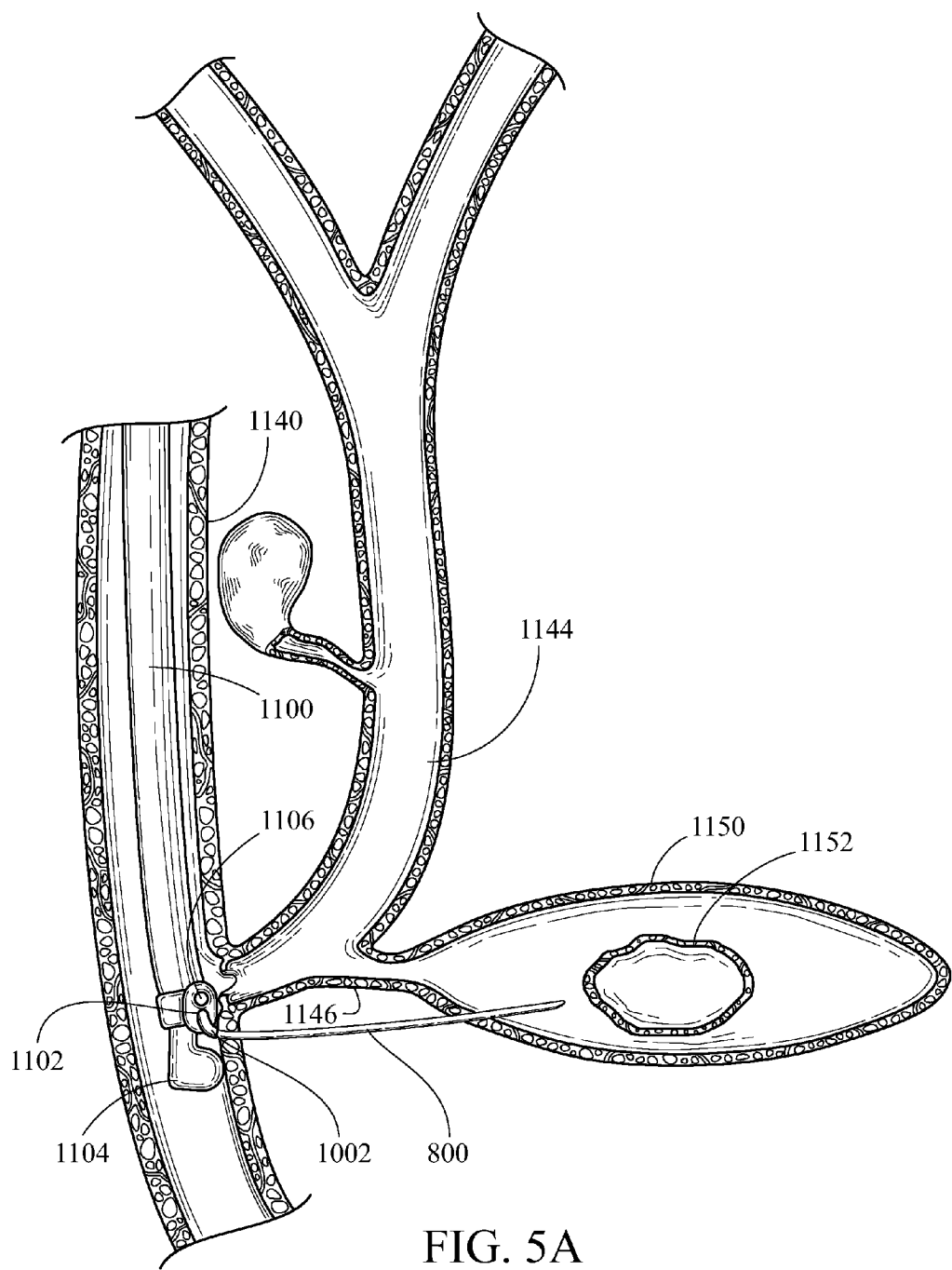
FIGS. 5A-5C show a method of placing fiducials.

The terms "proximal" and "distal" are used herein in the common usage sense where they refer respectively to a handle/doctor-end of a device or related object and a tool/patient-end of a device or related object.

A variety of fiducial and needle configurations may be used in keeping with the present embodiments including those described in U.S. Pat. No. 6,976,955 to Hardin, U.S. Pat. App. Publ. Nos. 2010/0280367, 2011/0152611 to Ducharme et al., 2013/0006101, 2014/0121677 to McHugo et al., 2013/0006286 to Lavelle et al., and 2013/0096427 to Murray et al.), each of which is incorporated herein by reference in its entirety (except that any definitions of terminology from the present application shall govern). One embodiment, illustrated with reference to FIGS. 2A-2C, of a fiducial 400 has a generally columnar body that is generally cylindrical with a generally circular transverse cross-section. A longitudinal surface face of the body may be dimpled to enhance its ability to reflect ultrasound waves and thereby provide a desirable echogenic profile. This dimpled characteristic may alternatively be embodied as a different irregular, patterned, or textured surface feature (e.g., knurled, ribbed) that may enhance the echogenicity of the fiducial 400, which will aid in visualizing it during EUS-guided placement, and allow it to be used in ultrasound visualization of a target site being marked by one or more fiducials 400 (e.g., a tumor).

Such a fiducial 400 preferably will be formed of a radio-opaque, non-ferromagnetic material such as, for example, gold, platinum, palladium, iridium, or alloys thereof, with one preferred embodiment including an alloy of palladium with rhenium (advantages of which may include desirable radio-opacity, market-price stability superior to gold, and ultrasound-reflectivity/echogenicity due to density). Being radio-opaque will allow the fiducial to be used in deployment techniques using fluoroscopy, as well as making it detectible/visualizable by radiographic means during a treatment or other procedure where it may be desirable to know the location(s) of one or more fiducials. Being non-ferromagnetic will lessen the likelihood that visualization techniques or other procedures employing magnetic fields such as, for example, MRI, will re-orient or otherwise dislodge a fiducial. Echogenic construction of a fiducial or needle may be enhanced by surface texture, but can also be provided by structural inclusions such as embedded bubbles or beads that provide for a different ultrasound reflectivity than material surrounding them. Fiducials may also be coated with a material (e.g., parylene) configured to reduce backscatter during radiography.

In a preferred embodiment, the fiducial 400 is configured and dimensioned for passage through and release from a needle lumen. For an endoscopic delivery system, the fiducial body 402 (exclusive of the protuberance) preferably will have an outer diameter (OD) of about the same or less than the inner diameter (ID) of a needle lumen, but the OD of the fiducial body preferably will be no greater than the needle ID. As used herein, the OD of the fiducial refers to an imaginary circle (or other geometric shape) whose outermost boundaries all fit within the ID of the needle lumen. In other words, it is preferable that the fiducial is dimensioned to fit slidably into the needle lumen, except the protuberance, which projects into the slot.

The longer body portion distal of the protuberance can help make certain that, during deployment through a needle, a first fiducial distal of this second fiducial will be fully advanced out of the needle before that second fiducial is positioned for deployment, as will be made clearer with reference to FIGS. 4-4B below. Accordingly, in many preferred embodiments, the fiducial protuberance (of the second and successive fiducials) will be nearer its proximal end than its distal end, so that the distal fiducial body portion projects sufficiently distally that it will advance the preceding first fiducial completely out of the needle lumen by the time that the second fiducial is in a position to be deployed (see FIGS. 4-4B, and corresponding text). It should be appreciated that, even if all surfaces of the central fiducial portion 402 and protuberance 408 are generally smooth, the preferred materials forming the fiducial 400 and the presence of the protuberance 408 may provide a desirable echogenic profile that is readily visualizable under ultrasound at a resolution sufficient for locating and/or navigating it in a patient's body.

The fiducial 400 has a generally cylindrical body 402 formed as a mass with a generally circular transverse cross-section along its proximal and distal end sections. A protuberance 408 projects from the longitudinal circumferential face of the fiducial body 402. As viewed from the top, the protuberance 408 is generally obround. The irregular shape and increased surface area (as compared to a typical cylindrical fiducial of the type used in plug-ended systems and/or systems with some type of lumen-occupying detent) preferably enhances the echogenicity of the fiducial, which preferably will already be desirably high due in part to its composition.

The protuberance 408 includes protuberance end faces 407 that may provide one or more of chamfered, filleted, and radiused transition to the outer face 406 of the body 402. The body 402 is generally a right cylinder, but for the protuberance 408. In this embodiment, the protuberance 408 is rounded and substantially parallel to the longitudinal central axis of the fiducial body, and it is about one half the length of the body 402, and it is centered along the body length. In a preferred embodiment, the fiducial 400 is configured and dimensioned for passage through and release from a needle lumen. For an endoscopic delivery system, the fiducial body (exclusive of the protuberance) will have an outer diameter (OD) of about the same or less than the inner diameter (ID) of a needle lumen, but the fiducial body OD preferably will be no greater than the needle ID. The protuberance 408 will engage and ride along through a needle slot.

Dimensions of one exemplary embodiment are also described with reference to FIGS. 2A-2C. In one exemplary embodiment the body 402 is about 0.12 inches (3.05 mm) long and has an OD of about 0.034 inches (0.86 mm). The protuberance 408 is about 0.06 inches (1.5 mm) long and is aligned along a midline of the body. The protuberance 408 projects about 0.008 inches (0.2 mm) above the OD of the body 402 and is about 0.011 inches (0.28 mm) wide. These measurements and proportions may be varied in other embodiments while remaining within the scope of the presently-claimed material. For example, the protuberance may be more distally or proximally located, and may be at an angle relative to the midline such that it partially spirals around the outer surface of the body.

FIG. 2C shows an end view of a transverse section taken along line 2C-2C of FIG. 2A. It shows one embodiment of general proportions of a fiducial body and protuberance of the present system.

FIG. 3 shows an embodiment of a fiducial introduction needle 800. The needle 800 is illustrated with a beveled distal tip 802. Its tubular cannula body 804 includes a longitudinal needle slot 806 along a distal end region of the cannula 804. The slot 806 preferably includes at least one detent including at least one detent surface, and more preferably two detents. The slot 806 is shown as being open through the entire wall of the cannula 804, but it should be appreciated that the slot may extend less than the thickness of the needle wall, such that it is embodied as a groove.

In the embodiment of FIG. 3, the detent is formed as a narrowed portion 807 of the slot 806 between two tabs 808. The tabs 808 are generally trapezoidal, but may have a different geometry in other embodiments. As shown in FIG. 3A, in certain preferred embodiments, the tabs 808 may be located immediately adjacent the distal bevel (e.g., to maximize efficiency of advancing a fiducial past them and out of the needle while minimizing residual overlap of a deployed fiducial with the beveled portion of the distal needle tip). Each of the transitions between the edge 806a of the needle slot 806, the proximal tab edge 808a, central tab edge 808b, and distal tab edge 808c may be cornered (e.g., chamfered or filleted) or rounded (e.g., radiused). The tabs 808 preferably are near the distal end of the slot 806. The detent does not impede the needle lumen, but serves to retain fiducials for user-controlled serial, one-at-a-time deployment.

The body wall cannula 804 generally circumferentially defines a needle lumen 810 configured to allow sliding passage therethrough of a fiducial such as, for example, a fiducial (e.g., as shown in FIGS. 2A-2C or others that would readily pass through the needle lumen 810, preferably with controllable retention of the fiducial(s) by the tabs 808). The needle may be constructed from a nickel-titanium alloy, cobalt-chromium (CoCr) alloy, stainless steel or any other suitable material. Its tip may have a different geometry than the beveled configuration shown. In an alternative embodiment, the tabs 808 may meet such that they will be forced to flex upward and/or outward to a greater degree to allow passage of a protuberance on a fiducial. And, the outer surface of the needle may be dimpled or otherwise textured to provide enhanced echogenicity.

An exemplary needle embodiment is also described with reference to FIG. 3, which exemplary needle embodiment may be configured and dimensioned for use with the exemplary fiducial embodiment described above with reference to FIGS. 2A-2C. In one such exemplary needle embodiment, the ID of the needle lumen is at least about 0.034 inches (0.86 mm). The OD of the needle is about 0.042 inches (1.07 mm; about 19-gauge), with a wall-thickness of about 0.008 inches (0.2 mm). The slot portion proximal of the tabs is about 0.02 inches (0.5 mm) wide and about 0.42 inches (about 10.7 mm) long. Each of the tabs extends about 0.06 inches (0.15 mm) out of the slot edge and has a slot-facing edge that is about 0.02 inches (0.5 mm) long (not including the proximal and distal angled transitions from the slot edge, which are radiused at about 0.005 inches (0.13 mm)). These measurements and proportions may be varied in other embodiments, including those illustrated herein, while remaining within the scope of the presently-claimed material. For example, the particular dimensions of a slot, tabs, and fiducial may be configured for use with a 22-gauge needle having a desirable balance of flexibility and stiffness, as well as including a distal needle tip bevel of about 30°, a slot width of about 0.014 inches (about 0.36 mm) with slot tabs separated only by about 0.006 inches (about 0.15 mm) across the slot, and echogenicity-enhancing surface dimpling disposed along the needle exterior adjacent and generally parallel with at least a distal length of the slot.

The distal end portion of a fiducial deployment system 1000 is described with reference to FIG. 4, which is an external view, FIG. 4A which is a longitudinal section view taken along line 4A-4A of FIG. 4, using the needle 800 and fiducial 400 described above, and FIG. 4B, which shows a transverse section view along a longitudinal axis of FIG. 4A. The system 1000 includes a flexible elongate needle sheath 1002. The needle 800, including a more flexible proximal body portion 820 extends through a sheath lumen 1004. At least one fiducial 400, illustrated here as a plurality of fiducials 400, is disposed slidably removably in a distal region of the needle lumen 810 of the needle's cannular body. The central longitudinal body portion 402 substantially occupies the inner diameter of the needle lumen 810. The protuberance 408 of each fiducial 400 has a height that may be about the same as the thickness of the needle wall, including the slot 806 into which the protuberances 408 project.

The protuberance 408 of the distal-most fiducial 400 is captured against the tabs 808 of the needle 800. A stylet 1006 configured for use as a pusher is disposed through a portion of the needle lumen 810 and preferably is configured for actuation from the proximal end, whereby it can be used to distally advance/push out the fiducials and/or hold them in place as the needle is withdrawn from around them. The presence of the fiducials and stylet in the needle 800 preferably improve its columnar strength and reduce the likelihood that it will get bent, crimped, or otherwise damaged as it is navigated through and out of the distal end of an endoscope working channel (not shown).

FIG. 4B shows a transverse section end view of a section of a needle 800 (as in FIG. 3) and a fiducial 400 (as in FIGS. 2A-2C). This view shows the preferred close tolerances and a preferred orientation of the fiducial body relative to the needle lumen 810 and the protuberance 408 relative to the needle slot 806.

Several different handle embodiments may be used to effect advancement and release of one or more fiducials. Certain handle embodiments are described with reference to FIGS. 6-7 below, including with reference to the structure and method described below with reference to FIGS. 4-4B and 5A-5C.

A method of using the fiducial deployment needle of FIGS. 4-4B is described with reference to FIGS. 5A-5C, with reference to the structures shown in greater detail in FIGS. 4-4B. In a preferred method of use, an endoscope 1100 is provided, including a working channel 1102. In one preferred method, the endoscope is an EUS endoscope including a distal ultrasound array 1104 configured for ultrasound imaging. The endoscope 1100 preferably also includes a video element 1106 (e.g., CCD, optical camera, or other means for optical visualization). The methods below are described with reference to placing fiducials 400 at the margins of a tumor 1152 of a patient's pancreas 1150, such that the needle body will be of sufficient length and navigability (e.g., pushability and flexibility) to perorally be directed through a patient's gastrointestinal tract to a target site, including doing so via a working channel of an endoscope such as a gastric endoscope, colonoscope, anuscope, or other visualization/procedure-assisting device.

Figure 5B:
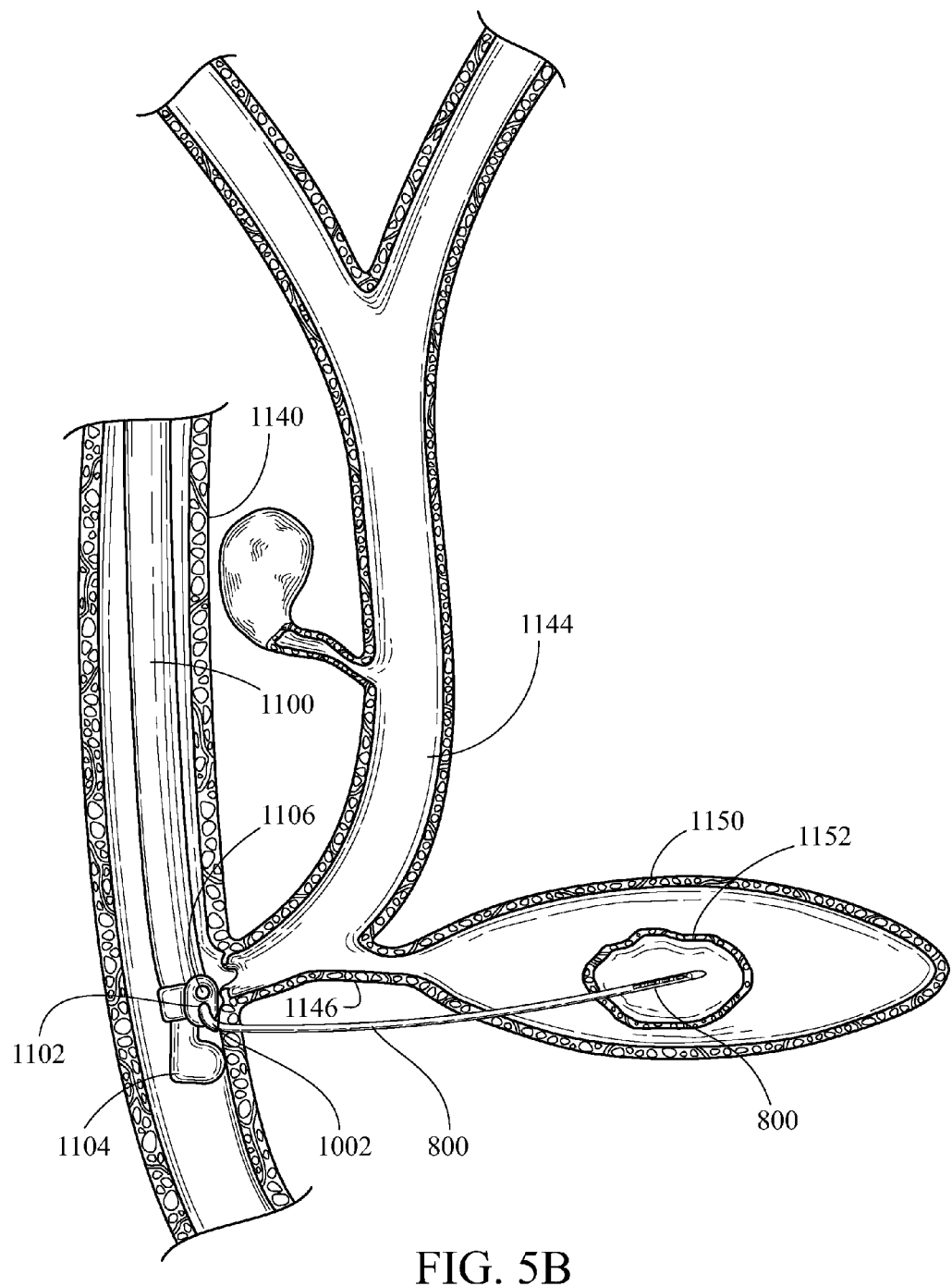
Figure 5C:
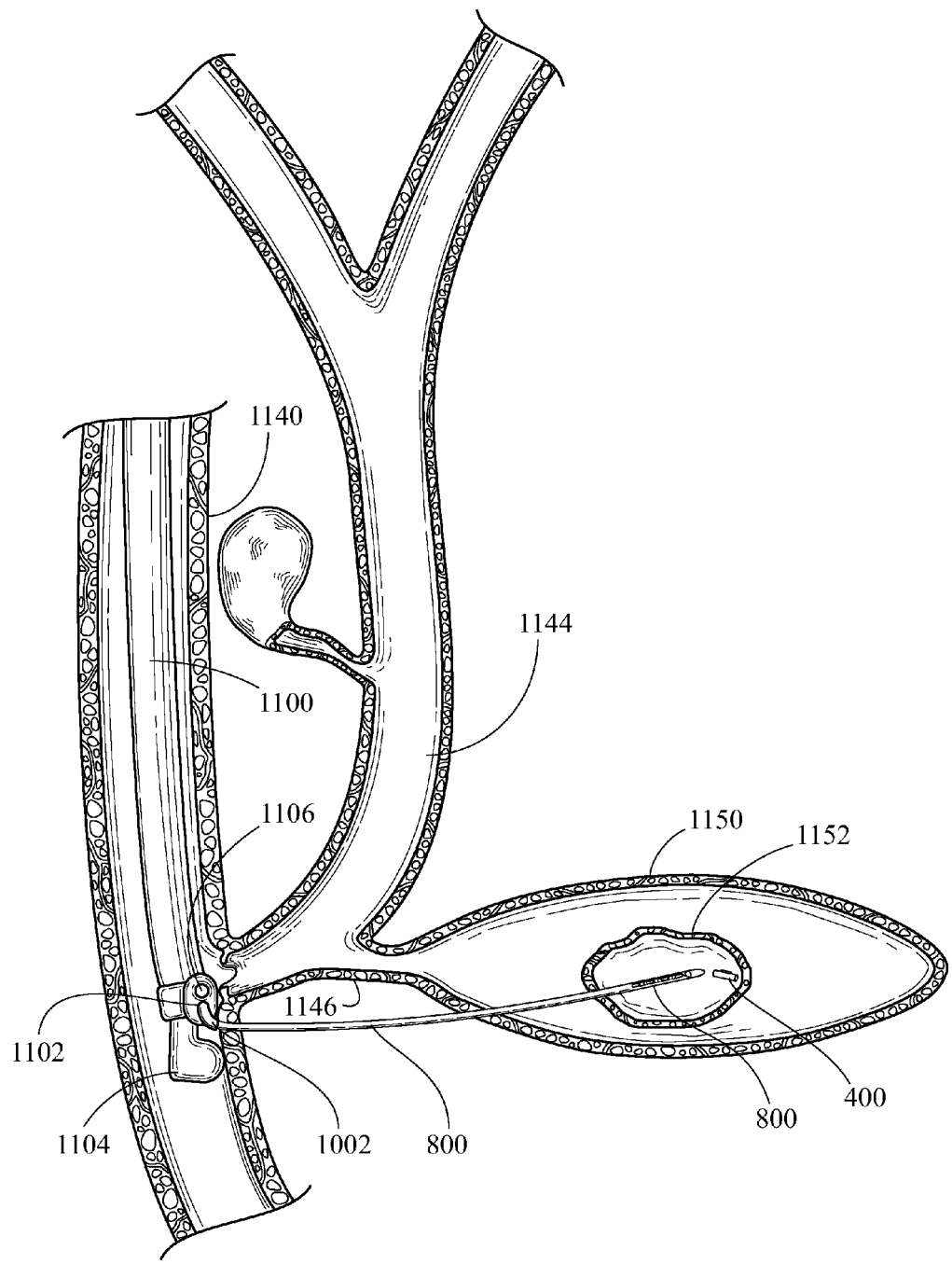

The endoscope 1100 is shown in FIG. 5A as having been directed through a patient's duodenum 1140 until its distal end portion is adjacent the Sphincter of Oddi, which provides access to the common bile duct 1144 from which the pancreatic duct 1146 branches and leads to the pancreas 1150.

As shown in FIG. 5A, the sheath 1002 has been advanced to the duodenal wall and the needle 800 has been pierced therethrough, extending near the pancreatic duct 1146 to a location adjacent the tumor 1152 in the pancreas 1150. As shown in FIG. 5B, the needle 800 is directed to a first target site at a margin of the tumor 1152 (preferably under ultrasound guidance, which can be replaced, complemented, and/or verified by fluoroscopy or another visualization technique). Once the distal end 802 of the needle 800 is positioned at the first target, the distal-most fiducial 400 therein is deployed. In one aspect, the deployment may be accomplished by positioning the distal needle end 802 and the fiducial 400 therein at the first target, then retracting the needle 800 while retaining the position of the stylet 1006 such that the fiducial 400 remains in the desired first target position. In another aspect, the deployment may be accomplished by positioning the distal needle end 802 and the fiducial 400 therein adjacent the first target, then holding the needle 800 in position while advancing the stylet 1006 such that the fiducial 400 is advanced into the desired first target position.

As will be appreciated from the structure of the needle 800 and fiducials 400 as shown in FIGS. 4-4B, a user preferably will be able to control advancement/deployment of the fiducials to one at a time, such that a plurality of fiducials (without any spacers) may serially but separately and independently-directed into different locations. When the fiducial 400 is in a "ready to deploy" position, a face of the distal protuberance 408 is engaged against the proximal tab edges 808a. To deploy the fiducial 400, the user must move one of the stylet 1006 or needle 800 relative to the other with sufficient force to advance the protuberance 408 through the tabs 808.

The user preferably will have a tactile sense of resistance as the protuberance 408 passes through the tabs 808, which resistance will decrease immediately as soon as the protuberance clears the tabs. Then the user preferably continues the relative motion of stylet and needle until resistance is again encountered, indicating that the next fiducial behind the distal-most one has met the proximal tab edges 808a.

It will often be preferred that the fiducials (and the protuberances thereon) be proportioned such that complete deployment of a distal-most fiducial includes it substantially clearing the distal needle tip 802 and coincides with the protuberance of the next distal-most fiducial meeting the proximal tab edges 808a. As such, it may be advantageous in some fiducial embodiments to position the protuberance more proximally on the fiducial body such that a fiducial body portion distal of the protuberance is longer than a body portion proximal of the protuberance. It should be appreciated that the protuberance of almost any fiducial embodiment in keeping with principles of the present invention may be disposed near the proximal end up to and including flush with the proximal end of the fiducial body. FIG. 5C shows the fiducial in place, with the needle withdrawn away from it.

Next, the user may retract the needle 800 into the sheath 1002 to a sufficient distance allowing it to be re-extended to a second target site, where the procedure described above may be repeated. These steps may be repeated for placement of third, fourth, and further fiducials. As is known in the art, these fiducials may be used for "positive targeting" and/or "negative targeting" of a therapy such as radiation therapy ("positive targeting" indicating "treat here", and "negative targeting" indicating "do not treat here"). The present system presents numerous advantages. For example, consider a patient already undergoing an endoscopy procedure to biopsy a located but undiagnosed tissue mass. The endoscopic biopsy can be taken and a tissue slide prepared immediately. If a diagnosis is made (in conjunction with whatever other data are available and pertinent) that the tissue mass will benefit from a treatment where placement of fiducials is indicated, the physician can immediately deploy fiducials in the manner described above.

The ability to complete the method using direct/video and ultrasound imaging with little or no use of fluoroscopy presents an advantage of minimizing the radiation exposure of the patient (who may, for example, have to undergo radiation therapies where the total amount of exposure to radiation is desired to be minimized to that which is therapeutically and diagnostically necessary). Advantages of time and expense for the patient, physician and other treating/diagnostic personnel, and the treatment facility are likely as implementation of the present method may prevent all of those entities from having to schedule and conduct a second endoscopic procedure, and/or to extend the initial diagnostic procedure with the time-consuming methods and materials currently available in the prior art as described. It should also be appreciated that, when informed by the present disclosure, those of skill in the art may utilize and/or adapt the presently-disclosed embodiments for percutaneous use while remaining within the scope of one or more claims.

Fiducials with generally cylindrical or otherwise generally regular geometry may migrate after having been placed in a desired location, including that—over the course of multiple treatments of a target area delineated by fiducials—they may migrate with changes in the condition of surrounding tissues. For circumstances where it may be advantageous to minimize migration, a fiducial may be used that includes one or more anchoring projections.

FIGS. 6A-6B show a handle embodiment 1600 that may be used with a fiducial deployment system. The handle 1600 includes a sheath-attached handle member 1602 with a needle-attached handle member 1604 longitudinally slidably disposed on its proximal end. A handle member 1606 (which may be configured for scope-attachment) is slidably attached to the distal end of the sheath-attached handle member 1602. The sheath-attached handle member 1602 is attached to the needle sheath 1612 and the needle-attached handle member 1604 is attached to the needle 1614 (which may be configured in the manner of any of the needles disclosed herein or later developed in accordance with principles of the present disclosure). The scope-attachment handle member 1606 is configured for incrementally fixable, longitudinally-adjustable (relative to the other handle components) attachment to the exterior of an endoscope working channel (not shown) using, for example, a threaded cavity 1616. The scope-attachment handle member 1606 allows a user to determine the distance by which the sheath 1612 will extend from a standard-length endoscope, and it may include numerical or other indicia 1617 corresponding to that relative length and an adjustable engagement structure 1618 allowing a user to select a length and engage the scope-attachment handle member 1606 accordingly. It should be appreciated that embodiments of the handle described and claimed herein may be practiced within the scope of the present invention without including a scope-attachment member.

The sheath-attached handle member 1602 includes numerical indicia 1608 and an adjustable ring 1609 that limits the movement of the needle-attached handle member 1604 and provides a way to select the distance to which the needle 1614 may be extended beyond the sheath 1612. By way of illustration, the configuration shown in FIG. 6A would allow the sheath to extend 5 units (e.g., inches, cm) beyond the distal end opening of an endoscope working channel, and the needle 1614 would not extend at all beyond the distal end of the sheath 1612. The configuration shown in FIG. 6B would allow the sheath to extend 3 units (e.g., inches, cm) beyond the distal end opening of an endoscope working channel, and the needle 1614 would be allowed to extend up to 6 units beyond the distal end of the sheath 1612, although its current position would be only about 4 units beyond the distal end of the sheath 1612.

A stylet 1610 extends through a lumen of the needle 1614 and has a stylet cap 1611 fixed on its proximal end. The stylet 1610 is shown as being retracted proximally in FIG. 6A, and extended beyond the distal end of the needle 1614 in FIG. 6B. The stylet 1610 may be manually advanced distally through the needle lumen in the same manner as described above (with reference to FIGS. 4-4B) for a stylet 1006. As such, a user may use the stylet to manually push fiducials out of a distal end of the needle 1614. If this method is used (e.g., in the manner described above for deployment of fiducials with reference to FIGS. 4-5C), a user may rely upon tactile feedback to determine when a fiducial has been advanced beyond any detents, which may be difficult through a long stylet—particularly if the detents are rounded such that the advancing motion is relatively smooth. Accordingly, it may be advantageous to provide an advancement mechanism configured to attach to (including being integrated with) the handle 1600 that provides improved control of stylet advancement.

Figure 7:
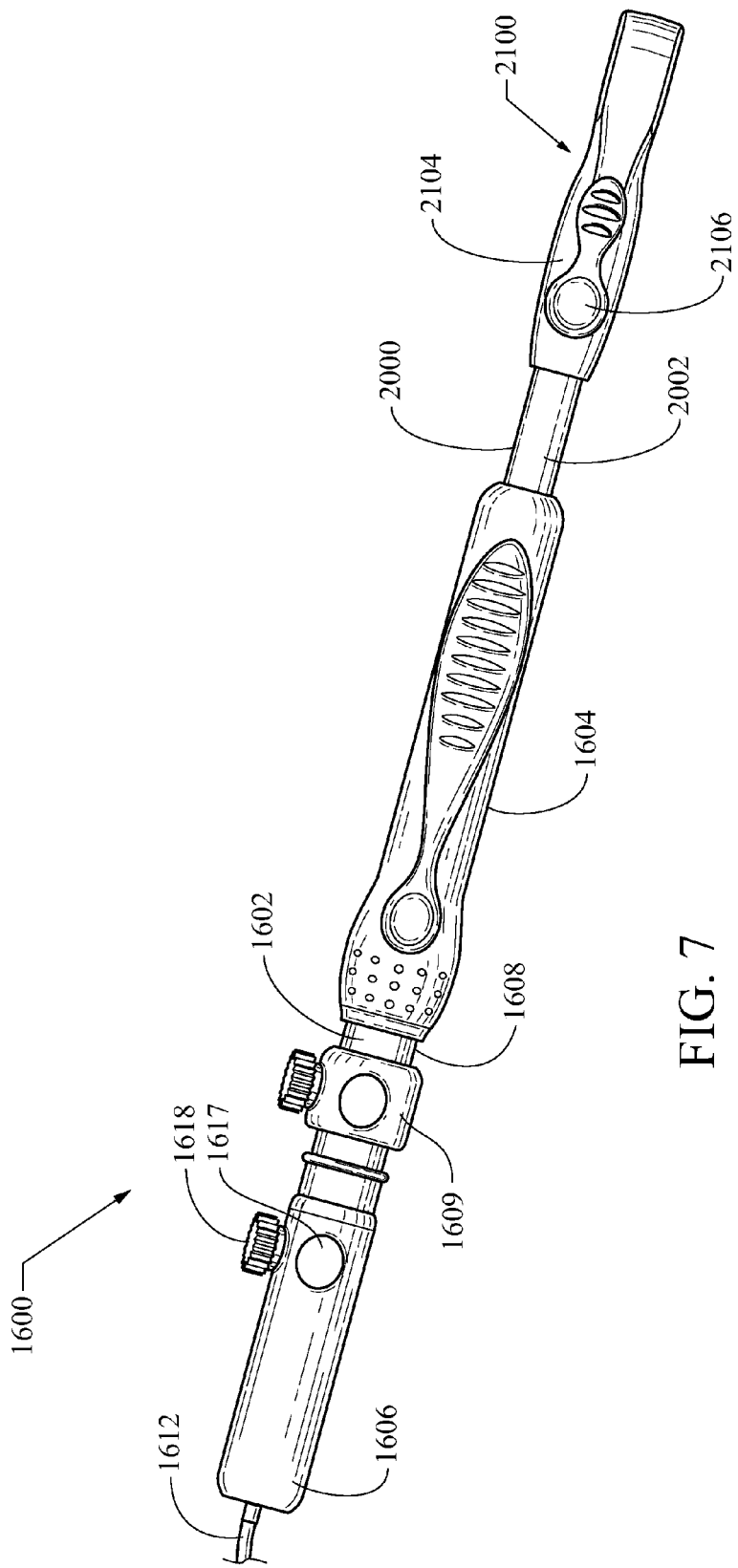
FIG. 7 shows a handle embodiment for a fiducial deployment system.

FIG. 7 shows another handle embodiment 1600 that may be used with a fiducial deployment system. The handle 1600 is shown in a closed configuration. The handle 1600 includes sheath-attached handle member 1602, needle-attached handle member 1604, handle member 1606, needle sheath 1612, needle 1614 (not shown, but which may be configured in the manner of any of the needles disclosed herein or later developed in accordance with principles of the present disclosure), numerical or other indicia 1617, adjustable engagement structure 1618, and adjustable ring 1609.

The handle 1600 may also include a guide sleeve 2000 connected to a proximal end of the needle-attached handle member 1604. The guide sleeve 2000 may have a generally cylindrical shape with a generally smooth outer surface 2002. A grasping handle 2100 may be proximal to the guide sleeve 2000 and engaged to move adjacent to the guide sleeve 2000, for example over the guide sleeve 2000. Grasping handle 2100 may include an inner surface 2102 (not shown), and an outer surface 2104 with an overmolded soft-touch portion 2106 to facilitate gripping by a user. A stylet 1610 (not shown) extends through a lumen of the needle 1614, and connects to an inner surface of the grasping handle 2100 on its proximal end. In this configuration, the stylet 1610 may also extend through needle-attached handle member 1604 and through guide sleeve 2000.

Figure 8:
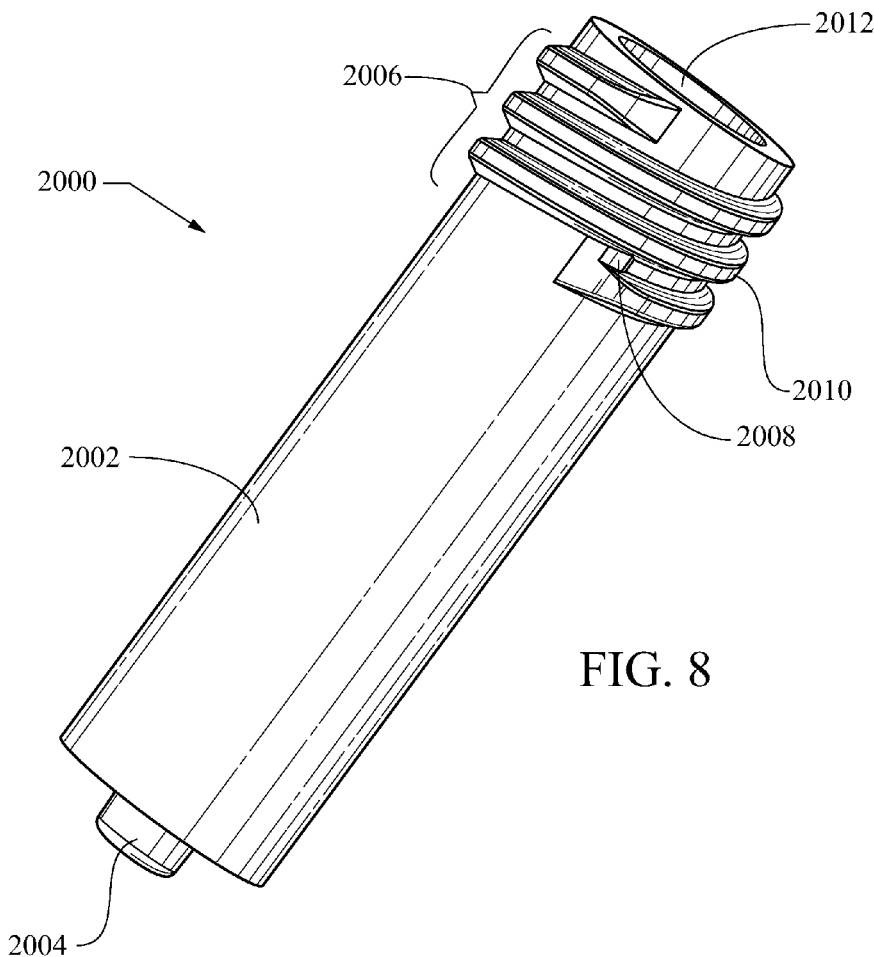
FIG. 8 shows a perspective view of a guide sleeve for a safety-catch mechanism for a fiducial deployment system.

FIG. 8 shows an expanded perspective view of guide sleeve 2000. The outer surface 2002 is generally smooth along a major length of guide sleeve 2000. This may enable the inner surface 2102 of grasping handle 2100 (illustrated in FIGS. 12-14) to slide over and along the smooth surface 2002 of the guide sleeve 2000. A cylindrical protrusion 2004 is located at a distal end of guide sleeve 2000. Protrusion 2004 may encompass needle 1614 and facilitate a connection between guide sleeve 2000 and needle-attached handle member 1604. For example, handle member 1604 may have a correspondingly indented surface to mate with cylindrical protrusion 2004 of the guide sleeve 2000, such that an adhesive could be applied to form a permanent attachment. Alternatively, a snap-fit mechanism, an ultrasonic weld, or other attachment means may be used, permanent or non-permanent.

The outer surface 2002 of guide sleeve 2000 may have a threaded surface 2006 made up of one or more threads 2010, for example at a proximal portion of guide sleeve 2000.

Alternatively, threaded surface 2006 may be located along a different portion of guide sleeve 2000, for example near the mid-point, or on an inner surface 2012. In an alternative embodiment, the threads 2010 of threaded surface 2006 may comprise one or more circumferential threads and/or partial threads.

At least one safety-catch structure 2008 may be disposed on the guide sleeve 2000. The function of the safety catch structure is to prevent unintentional stylet advancement and/or fiducial deployment, for example during manufacturing, shipping, and handling immediately prior to use. The safety-catch structure may be disposed between threads 2010 of the threaded surface 2006.

Figure 9:
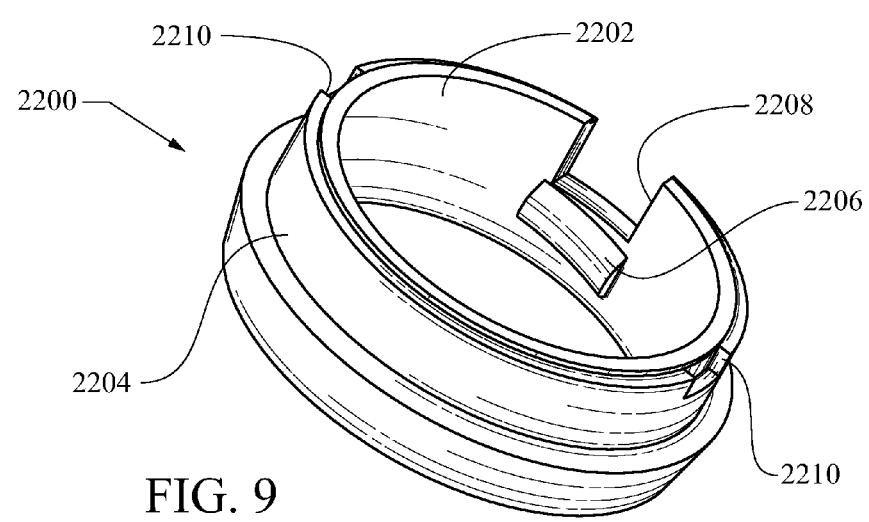
FIGS. 9-11 show, a collar for a safety-catch mechanism for a fiducial deployment system from, respectively, a perspective view, bottom view, and top view.
Figure 10:
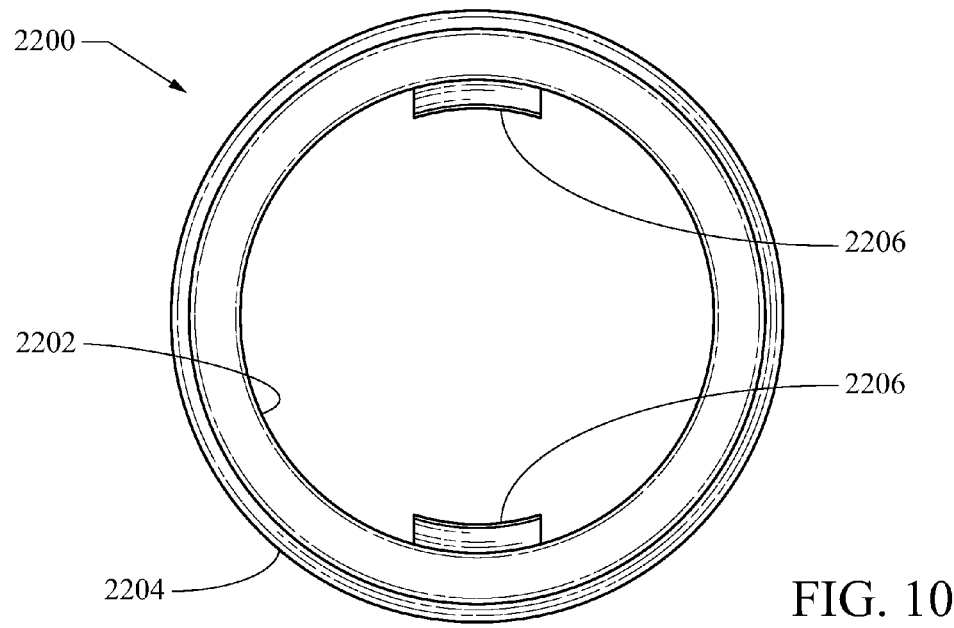
Figure 11:
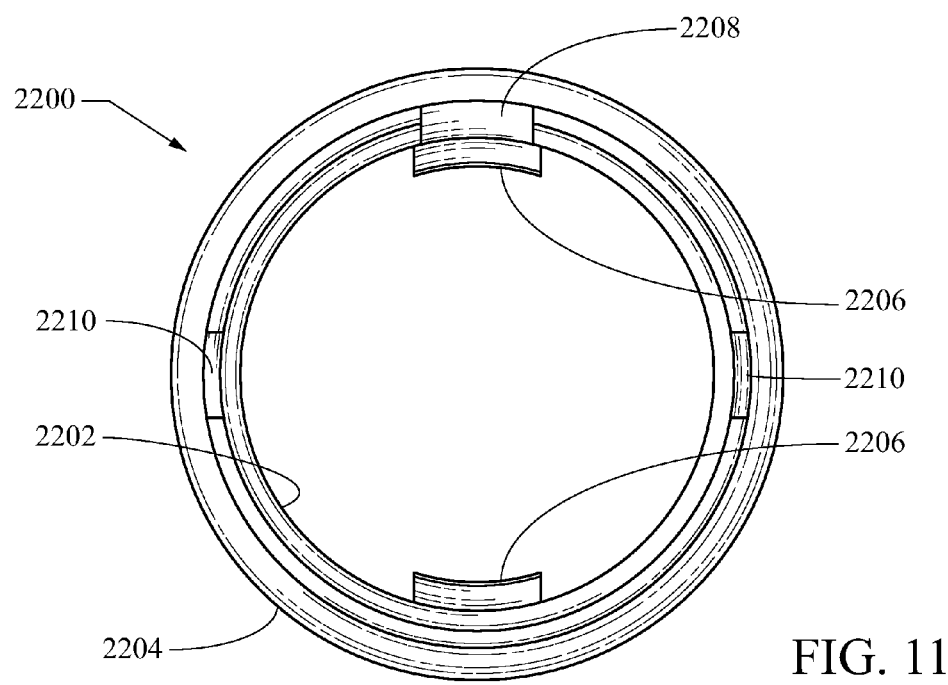

FIGS. 9-11 and FIG. 15 show a collar 2200 that at least partially fits within grasping handle 2100. FIGS. 9-11 show a collar 2200 in an expanded perspective view, a bottom view (from a distal end looking proximally), and a top view (from a proximal end looking distally), respectively. Collar 2200 may have an inner surface 2202 with one or more protruding tabs 2206, an outer surface 2204 with at least one recess 2210, and at least one notch 2208 extending therebetween.

Figure 12:
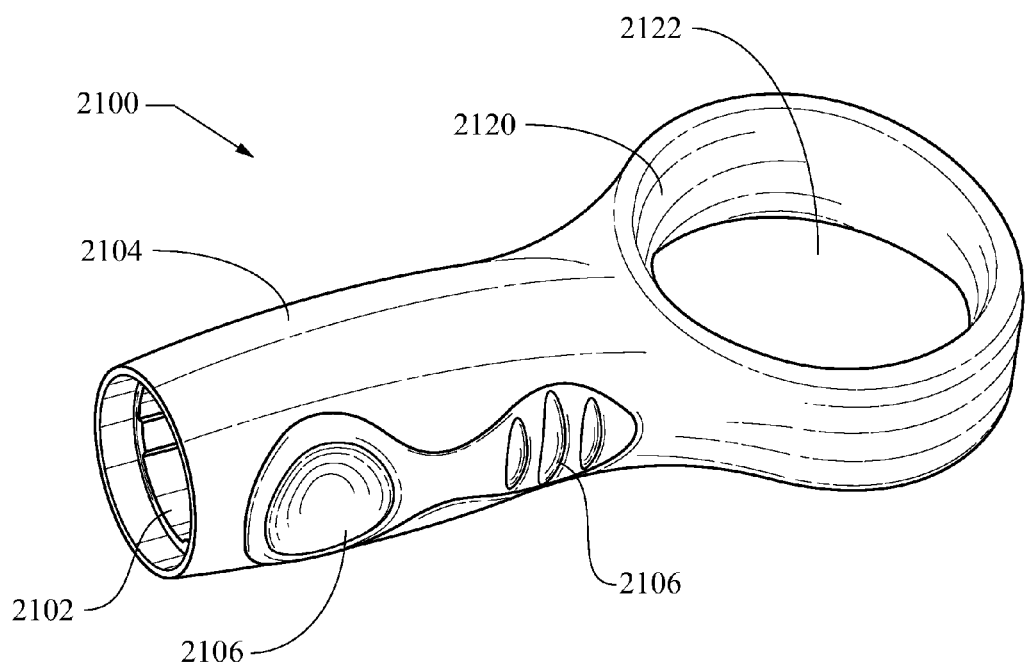
FIGS. 12-14 show a grasping handle for a safety-catch mechanism for a fiducial deployment system from, respectively, a perspective side view, a perspective bottom view, and a bottom view.
Figure 13:
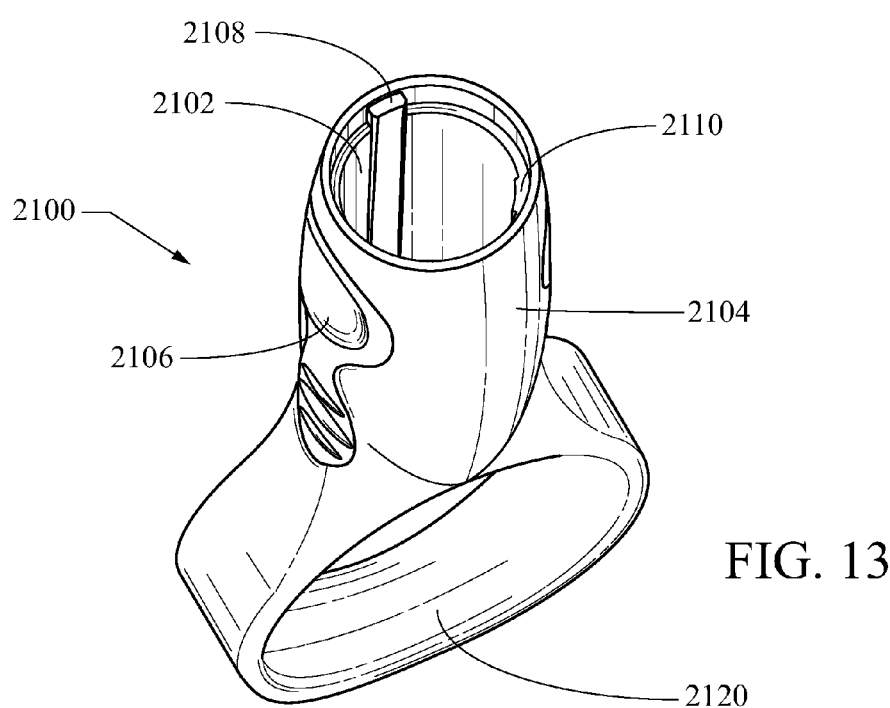
Figure 14:
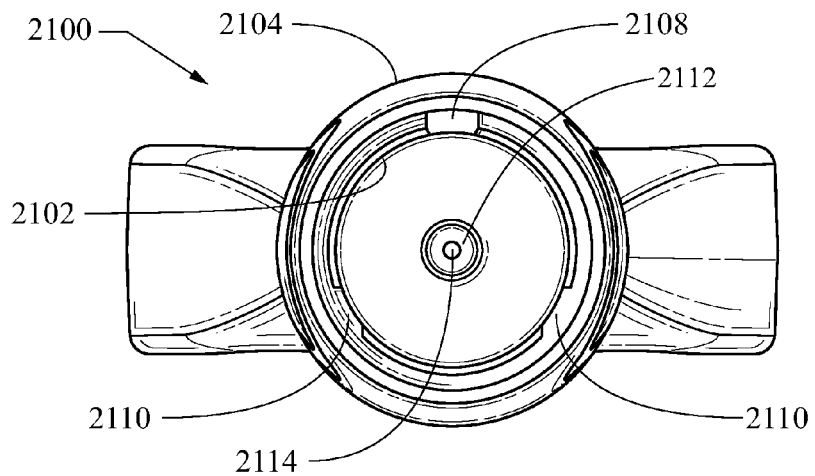

FIGS. 12-14 show the grasping handle 2100 in a side perspective view, a bottom perspective view (from a distal end looking proximally), and a bottom end view, respectively. Grasping handle 2100 may have an inner surface 2102 with at least one major rib 2108, at least one minor rib 2110, and a stylet base 2112 having a stylet hole 2114 sized to fit the proximal tip of stylet 1610. Grasping handle 2100 may have an outer surface 2104 with an overmolded soft-touch portion 2106 to facilitate gripping by a user, and a thumb ring 2120 having a thumb ring hole 2122. The thumb ring 2120 and thumb ring hole 2122 may be sized to fit a variety of fingers. A person of skill in the art will recognize that other shapes and configurations for gripping the grasping handle 2100 are also considered.

Collar 2200 may be constructed and dimensioned to attach to the inner surface 2102 of grasping handle 2100, for example by using an adhesive, a snap-fit mechanism, or other attachment means. The at least one notch 2208 may be a rectangular notch in the body of collar 2200, extending from the inner surface 2202 to the outer surface 2204. The at least one major rib 2108 on the inner surface 2102 of grasping handle 2100 may be correspondingly sized to receive the at least one notch 2208. This may facilitate adhesive connection and may ensure a consistent alignment of the collar 2200 within the grasping handle 2100. Similarly, the at least one minor rib 2110 may be correspondingly sized to receive the at least one recess 2210. This may facilitate both adhesive connection and proper alignment within the inner surface 2102 of grasping handle 2100. For example, as shown in FIGS. 9-14, the collar 2200 would only fit within the grasping handle 2100 in a configuration where the notch 2208 aligned with the major rib 2108, and the two recesses 2210 aligned with the two minor ribs 2110. Other embodiments are also considered, for example, the number, size, and shape of notches 2208, recesses 2210, major ribs 2108, and minor ribs 2110 may vary.

The one or more protruding tabs 2206 on the inner surface 2202 of collar 2200 may be protruding tabs as shown in FIG. 9, but may also be circumferential threads (not shown) or a partial thread (not shown). The one or more protruding tabs 2206 may be sized to slidably rotate between the threads 2010 of threaded surface 2006 of guide sleeve 2000, however, they may also be sized so as to not freely rotate over (or otherwise overcome) the at least one safety-catch structure 2008, as described below.

The proximal tip of stylet 1610 may be securely seated in the stylet hole 2114 of stylet base 2112, for example by using an adhesive. This connects the stylet 1610 to the grasping handle 2100 and collar 2200, such that all three components move as one.

Figure 15:
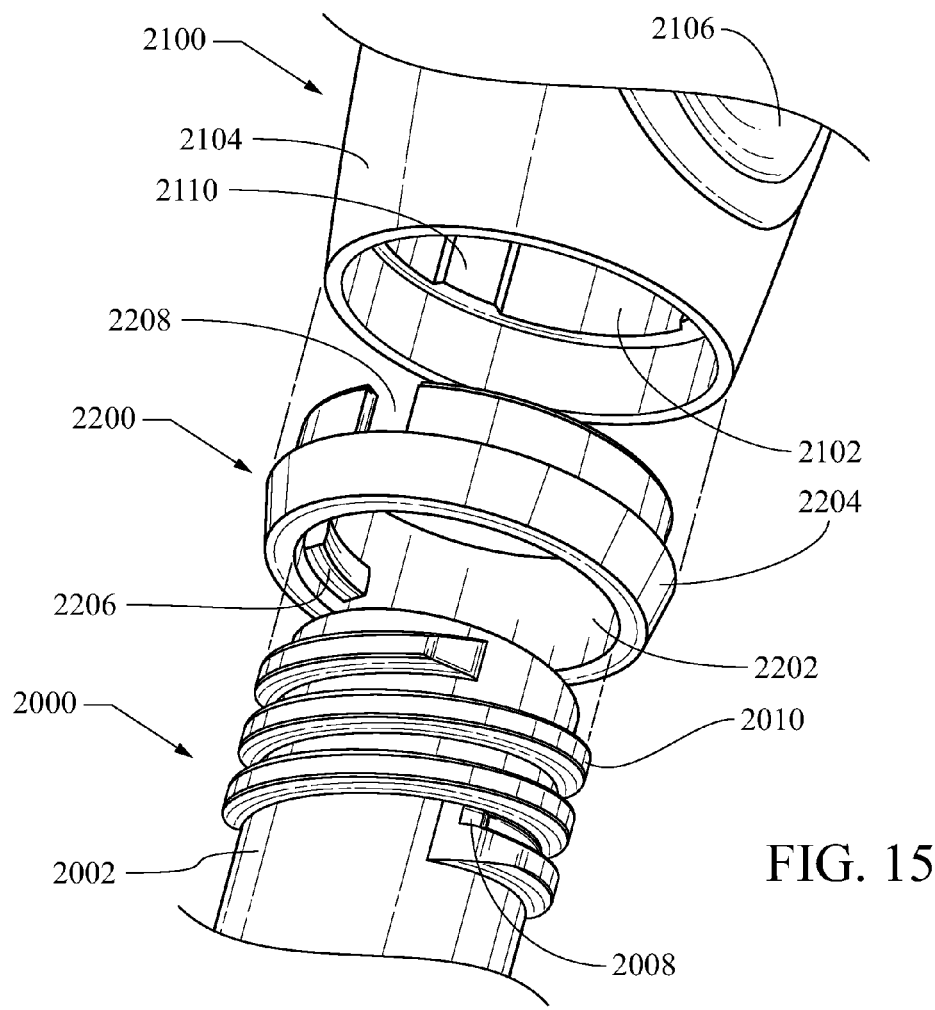
FIG. 15 shows a safety-catch mechanism for a fiducial deployment system in a perspective expanded view.

FIG. 15 shows the three major components of the safety-catch mechanism, the guide sleeve 2000, collar 2200, and grasping handle 2100. As shown and described, the collar 2200 may attach to the inner surface 2102 of the grasping handle 2100, and the one or more protruding tabs 2206 may engage with the threads 2010 of threaded surface 2006 of guide sleeve 2000.

This embodiment may include a safety-catch mechanism. The safety-catch structure 2008 may utilize a locking-unlocking mechanism to prevent the premature deployment of fiducials, for example during manufacturing, shipping, and handling immediately prior to use. As described above, the stylet 1610 is connected to the grasping handle 2100 which is connected to the collar 2200 having one or more protruding tabs 2206. These one or more protruding tabs 2206 may be sized to slidably rotate between the threads 2010 of threaded surface 2006 of guide sleeve 2000. However, the one or more protruding tabs 2206 may also be sized such that protruding tabs 2206 do not freely rotate over the at least one safety-catch structure 2008. For example, safety-catch structure 2008 could be a bump detent on the outer surface 2002 of guide sleeve 2000 between two threads 2010 of threaded surface 2006, as shown in FIGS. 8 and 15. The safety catch embodiments shown and described with reference to FIGS. 7-15 (and any equivalents) will effectively prevent unintentional stylet advancement and/or fiducial deployment.

In such a configuration, the grasping handle 2100 and collar 2200 having one or more protruding tabs 2206 could freely rotate past some but not all threads 2010 of threaded surface 2006. However, this free rotation could not continue once the one or more protruding tabs 2206 reach the at least one safety-catch structure 2008, unless the one or more protruding tabs 2206 physically overcomes the at least one safety-catch structure 2008. In order to overcome the at least one safety-catch structure 2008, the user would have to apply a mechanical force to the grasping handle 2100. This force would have to exceed a threshold such that either or both of the safety-catch structure(s) 2008 and the protruding tab(s) 2206 deform, allowing the protruding tab(s) 2206 to rotate past the safety-catch structure(s) 2008. This threshold may be a torque applied to the grasping handle 2100, for example, a threshold of less than about 1.5 inch-pounds. At a minimum, the threshold may be high enough so that a user could feel a tactile resistance or "bump" when the one or more protruding tabs 2206 engage the at least one safety-catch structure 2008. This may also be high enough so that the resistance isn't overcome during manufacturing, shipping, or handling. Overcoming this resistance may also signal to the user that the stylet 1610 is "ready to deploy." Additionally, the resistance may prevent the user (physician) from deploying fiducials prematurely, for example if the user inadvertently moves the grasping handle 2100.

A person of skill in the art will recognize that this unlocking step is reversible. After the device is "ready to deploy," a user may wish to re-lock the device using the safety-catch mechanism. This is easily accomplished by rotating the grasping handle in the opposite direction until the protruding tab(s) 2206 again overcome the safety-catch structure 2008, this time from the opposite side.

After rotating past the at least one safety-catch structure 2008, the grasping handle 2100 and hence the stylet 1610 may be in a "ready to deploy" position where it is free to move distally. For example, as shown in FIG. 15, the safety-catch structure 2008 is at a distal end of the threaded surface 2006, such that after this structure is overcome, the grasping handle 2100 can freely slide distally along the smooth outer surface 2002 of guide sleeve 2000, moving the stylet 1610 and fiducials 400 distally. The guide sleeve keeps the stylet 1610 straight even if the user's grip is slightly offset, therefore ensuring smooth advancement of the stylet 1610 and fiducials 400.

In use, the handle 1600 may allow a physician to deploy fiducials 400 during a therapeutic procedure. A physician may grasp the first handle 1604 and the grasping handle 2100, and apply a torque to rotate the grasping handle 2100. The physician may continue turning until she feels a "bump" or resistance. This signals that at least one of the protruding tabs 2206 are in contact with at least one safety-catch structure 2008. The physician may then apply additional torque to the grasping handle 2100 until this resistance is overcome. Then the grasping handle 2100 will be free to rotate and slide distally along the guide sleeve 2000. The physician may then apply pressure to move the grasping handle 2100 in a distal direction along the smooth outer surface 2002 of guide sleeve 2000. Since the grasping handle 2100 is connected to the stylet 1610, this movement also advances the stylet in a distal direction, thereby advancing one or more fiducials in a distal direction at or near the tip of needle 1614. Once advanced far enough, the fiducials will leave the tip of the needle one-by-one to remain in the targeted tissue. The physician may control this distal movement by varying the amount of force applied to the grasping handle 2100. Distal movement may also be limited by the various locking structures 1618 and 1609, as well as the length of the guide sleeve 2000 relative to the grasping handle 2100 since one component slides within the other. The physician may also reposition the needle as needed to deploy in another location.

Alternative embodiments for the safety-catch structure 2008 are also considered. For example, a bump detent 2008 could be located upon the threads 2010 of threaded surface 2006, and/or on the one or more protruding tabs 2206 of the collar. The geometry of the bump detent may vary, for example it may be circular, spherical, rectangular, chamfered, or other known shapes. Alternatively, the threads 2010 of threaded surface 2006 and/or the one or more protruding tabs 2206 could have a narrowing or choke point such that the threads passing through this point would encounter resistance.

Those of skill in the art should appreciate that there are many ways to manufacture and assemble the embodiments described. For example, the guide sleeve 2000, grasping handle 2100, and collar 2200 may each be injection molded. If the grasping handle 2100 has an overmolded soft-touch 2106, there will be two molds for this component, a pre-mold and an overmold. If the wire comprising the stylet 1610 is insert-molded into the grasping handle 2100, there will be additional tooling required. A cannula within the grasping handle will need to be secured to the stylet 1610 wire before insert molding. This can be done with a bead weld, crimp, adhesive, or other means of secure attachment.

Each of the components may or may not be made of different polymers. The stylet 1610 may be made from nitinol of length approximately equal to that of the needle, and inserted into the inner diameter of a stainless steel cannula of approximately 13 cm. The stainless steel cannula provides stability to the proximal portion of the stylet 1610. The stainless steel cannula and nitinol stylet 1610 are then insert-molded into the stylet hole 2114 of the grasping handle 2100 pre-mold. After the pre-mold, the soft-touch overmold may be added for aesthetic appeal and/or ergonomic effect.

After the grasping handle 2100 is complete, the collar 2200 is assembled on the distal part of the grasping handle 2100. There is a small gap between the outer surface 2204 of the collar 2200 and the inner surface 2102 of the grasping handle 2100 which allow for the use of adhesive to secure the parts. In some embodiments, instead of adhesive, the design could be modified for attachment via ultrasonic welding, snap-fit, etc.

The notch 2208 and major rib 2108 guide the assembler to align the grasping handle 2100 and collar 2200 into the only possible configuration relative to each other. After the grasping handle 2100 and collar 2200 assembly is complete, they are assembled with the guide sleeve 2000. The threads 2010 of guide sleeve threaded surface 2006 engage the partial threads or protruding tabs 2206 of the collar 2200. The assembler may thread the grasping handle 2100 and collar 2200 onto the guide sleeve 2000 until she feels a "bump." The assembler should not overcome the "bump," but leave the guide sleeve 2000 and grasping handle 2100 in this configuration for packaging and shipping.

One advantage to molding the collar 2200 and grasping handle 2100 separately is molding feasibility. If the collar 2200 and grasping handle 2100 were molded as one piece, such a design would include an undercut feature to form the one or more protruding tabs 2206 of the collar 2200 directly on the inner surface 2102 of the grasping handle 2100. Since the tooling for an undercut feature may be more complicated and expensive, creating two distinct components (collar 2200 and grasping handle 2100) that are attachable may achieve a more complex or otherwise desirable design at a cheaper tooling cost. Alternatively, in other manufacturing environments such as 3D-printing, the collar 2200 and grasping handle 2100 may be formed as one piece.

Those of skill in the art will appreciate that the relative orientation/position of the interfacing and overcomeable-stop structures of the guide sleeve and the grasping handle may readily be reversed as a mechanical equivalent, albeit not explicitly illustrated in the present drawings. For example, a threaded surface or protruding tab may be on an inner body instead of an outer body or vice-versa, or on the guide sleeve instead of the collar, or vice-versa.

The safety-catch mechanism described in this embodiment may be used with any appropriate control mechanism for deploying fiducial, including but not limited to, mechanisms such as one-click per turn, pin-click, and clutch/gear. Other handle configurations include, for example, those disclosed in U.S. Pat. No. 6,613,002, U.S. Pat. No. 6,976,955, U.S. Pat. App. Publ. Nos. 2010/0280367, 2011/0152611, 2010/059641 to Ducharme et al., 2013/0006101 to McHugo et al., 2013/0006286 to Lavelle et al., and 2013/0096427 to Murray et al., each of which is incorporated herein by reference in its entirety (except that any definitions of terminology from the present application shall govern).

Drawings and particular features in the figures illustrating various embodiments are not necessarily to scale. Some drawings may have certain details magnified for emphasis, and any different numbers or proportions of parts should not be read as limiting, unless so-designated by one or more claims. Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. For example, a needle and fiducials of the present system may be used percutaneously, including in another minimally invasive surgical procedure, such as a laparoscopic-type procedure, within the scope of the claimed invention. For example, a target site may be a location in or near the gastrointestinal tract (e.g., liver, pancreas) such as those locations that may be accessible by endoscopy (using a minimally invasive endoscope introduced through a natural patient orifice, e.g., mouth, anus, vagina). This includes—more broadly—sites reachable through NOTES (natural orifice translumenal endoscopic surgery) procedures. The present method and device may also be used with other minimally-invasive surgical techniques such as percutaneous endoscopic procedures (e.g., laparoscopic procedures) or percutaneous non-endoscopic procedures, but most preferably is used with less invasive endoscopy procedures. It is therefore intended that the foregoing detailed description be regarded as illustrative rather than limiting. And, it should be understood that the following claims, including all equivalents, are intended to define the spirit and scope of this invention.

We claim:

1. A safety-catch mechanism for a fiducial-deployment system, comprising:
    an elongate first handle member defining a central longitudinal axis and handle lumen;
    a guide sleeve proximal to the first handle member;
    a grasping handle proximal to the guide sleeve and engaged movably adjacent to the guide sleeve;
    where one of the guide sleeve or the grasping handle includes a threaded surface on a portion thereof;
    where the other of the guide sleeve or the grasping handle includes one or more protruding tabs on a portion thereof constructed and dimensioned to engage rotatably between threads of the threaded surface;
    a stylet connected to the grasping handle and extending through at least a portion of the guide sleeve and the first handle member, along or generally aligned with the central longitudinal axis; and
    at least one safety-catch structure disposed between threads of the threaded surface.

2. The safety-catch mechanism of claim 1, wherein the at least one safety-catch structure is constructed and dimensioned to resist distal stylet motion when one of the protruding tabs contacts the at least one safety-catch structure and less than a threshold amount of mechanical force is applied to the grasping handle, and where said construction provides that mechanical force exceeding said threshold moves the one of the protruding tabs past the at least one safety-catch structure, thereby permitting further distal stylet movement.

3. The safety-catch mechanism of claim 1, further comprising a fiducial deployment needle retaining a plurality of fiducials for distal deployment in a controlled serial manner, where the stylet is disposed through a lumen of said needle and is effectively but overcomeably prevented from contacting the fiducials by the safety-catch structure.

4. The safety-catch mechanism of claim 1, wherein the at least one safety-catch structure is a bump detent.

5. The safety-catch mechanism of claim 4, wherein the bump detent is a geometric shape selected from the group consisting of a circular face, a spherical face, a rectangular face, and a chamfered face.

6. The safety-catch mechanism of claim 1, wherein the grasping handle includes a thumb ring.

7. The safety-catch mechanism of claim 6, wherein the thumb ring comprises a soft-touch overmold.

8. The safety-catch mechanism of claim 1, wherein the threaded surface is on a proximal portion of the guide sleeve and the one or more protruding tabs engaging the threads are on a distal portion of the grasping handle.

9. The safety-catch mechanism of claim 8, wherein the threaded surface is on an outer surface of the guide sleeve, and the one or more protruding tabs engaging the threads are on an inner surface of the grasping handle.

10. The safety-catch mechanism of claim 1, wherein the grasping handle is formed from at least two pieces.

11. The safety-catch mechanism of claim 10, wherein the at least two pieces comprise a collar and a thumb ring.

12. The safety-catch mechanism of claim 11, wherein the at least two pieces are attached using an attachment mechanism selected from the group consisting of an adhesive, a snap-fit, a weld, and an ultrasonic weld.

13. The safety-catch mechanism of claim 10, wherein one of the at least two pieces includes a rib and another of the at least two pieces includes a notch, both sized such that the rib fits within the notch.

14. The safety-catch mechanism of claim 10, wherein one of the at least two pieces includes a rib and another of the at least two pieces includes a recess, both sized such that the rib fits within the recess.

15. The safety-catch mechanism of claim 1, wherein the threshold amount of mechanical force is about 1.5 inch-pounds.

16. The safety-catch mechanism of claim 1, wherein the at least one safety-catch structure between threads of the threaded surface is configured as a narrowed section of threads.

17. The safety-catch mechanism of claim 1, wherein the grasping handle is engaged movably over the guide sleeve.

18. The safety-catch mechanism of claim 1, wherein the one or more protruding tabs are configured as circumferential threads that engage the threaded surface.

19. A safety-catch mechanism for a fiducial-deployment system, comprising:
    an elongate first handle member having a central longitudinal axis and attached to a guide sleeve;
    a stylet attached to a grasping handle and extending through at least a portion of the guide sleeve and the first handle member, along or generally aligned with the central longitudinal axis,
    wherein the grasping handle is movably engaged to the guide sleeve,
    wherein grasping handle and guide sleeve each have a portion of a safety-catch mechanism that engages another portion of the safety catch mechanism, and
    wherein the safety-catch mechanism includes at least one safety-catch structure and at least one protruding tab constructed and dimensioned to traverse over and across the safety-catch structure when mechanical force exceeding a threshold moves at least one protruding tab past at least one safety-catch structure.

20. A stylet-advancement system, comprising:
    an elongate first handle member having a handle lumen;
    a guide sleeve proximal to the first handle member;
    a grasping handle engaged movably to the guide sleeve;
    a stylet connected to the grasping handle and extending through at least a portion of the guide sleeve and the first handle member,
    at least one safety-catch means for preventing unintentional stylet advancement, wherein the safety-catch means includes at least one bump detent and at least one protruding tab constructed and dimensioned to traverse over and across the bump detent when mechanical force exceeding a threshold moves at least one protruding tab past at least one bump detent.

\* \* \* \* \*